(12) United States Patent  (10) Patent No.: US 8,783,247 B2
Newman, Jr.  (45) Date of Patent: Jul. 22, 2014

(54) PRESSURE RELEASE SYSTEMS, APPARATUS AND METHODS

(75) Inventor: Lionel Newman, Jr., Los Angeles, CA (US)

(73) Assignee: Wet Nose Technologies, LLC., Los Angeles, CA (US)

( * ) Notice: Subject to any disclaimer, the term of this patent is extended or adjusted under 35 U.S.C. 154(b) by 935 days.

(21) Appl. No.: 12/700,219

(22) Filed: Feb. 4, 2010

(65) Prior Publication Data

US 2010/0282253 A1 Nov. 11, 2010

Related U.S. Application Data

(60) Provisional application No. 61/149,875, filed on Feb. 4, 2009.

(51) Int. Cl.
*A61M 16/00* (2006.01)
*A62B 9/02* (2006.01)

(52) U.S. Cl.
USPC ............. 128/202.22; 128/204.18; 128/205.24

(58) Field of Classification Search
USPC ............. 128/200.24, 202.22, 204.18, 204.12, 128/205.23, 205.24; 137/908
See application file for complete search history.

(56) References Cited

U.S. PATENT DOCUMENTS

| 1,304,327 A | 5/1919 | Klay |
|---|---|---|
| 1,314,855 A | 9/1919 | Carpenter |
| 1,889,425 A | 11/1932 | Sorensen |
| 2,088,720 A | 8/1937 | Poliniak |
| 2,295,528 A | 9/1942 | Cutter et al. |
| 2,328,995 A | 9/1943 | Olds |
| 2,375,711 A | 5/1945 | Vondrak |
| 2,422,702 A | 6/1947 | Rodanet |
| 2,449,497 A | 9/1948 | McLeod |
| 2,812,765 A | 11/1957 | Tofflemire |
| 3,065,749 A | 11/1962 | Brass |
| 3,710,780 A | 1/1973 | Milch |
| 3,749,090 A | 7/1973 | Stewart |

(Continued)

FOREIGN PATENT DOCUMENTS

| EP | 0979660 A | 2/2000 |
|---|---|---|
| EP | 1084727 | 4/2006 |

(Continued)

OTHER PUBLICATIONS

OA dated Sep. 29, 2009 for U.S. Appl. No. 11849268, 19 pages.

(Continued)

*Primary Examiner* — Nicholas Lucchesi
*Assistant Examiner* — Leah Stohr
(74) *Attorney, Agent, or Firm* — Amin, Turocy & Watson, LLP

(57) ABSTRACT

A respiratory circuit apparatus and circuit are provided. The circuit includes: an adapter having a plurality of connectors of two or more different internal or outer diameters; and a pressure release valve configured to emanate sound if a pressure of a gas received at the pressure release valve is greater than or equal to an activation pressure of the pressure release valve. The pressure release valve can have a first end of a body portion coupled with one of the plurality of connectors of the adapter. The pressure release valve can be coupled inline in the respiratory circuit via the adapter and in close proximity to a patient location.

19 Claims, 23 Drawing Sheets

(56) References Cited

U.S. PATENT DOCUMENTS

| | | | |
|---|---|---|---|
| 3,804,089 A | | 4/1974 | Bridgman |
| 3,807,445 A | * | 4/1974 | McPhee .................. 137/557 |
| 3,827,433 A | | 8/1974 | Shannon |
| 3,949,749 A | | 4/1976 | Stewart |
| 3,972,326 A | | 8/1976 | Brawn |
| 4,080,989 A | | 3/1978 | Chapelsky et al. |
| 4,164,219 A | * | 8/1979 | Bird .................. 128/204.19 |
| 4,215,476 A | | 8/1980 | Armstrong |
| 4,299,221 A | | 11/1981 | Phillips et al. |
| 4,459,983 A | | 7/1984 | Beyreuther et al. |
| 4,464,316 A | | 8/1984 | Michaels |
| 4,468,216 A | | 8/1984 | Muto |
| 4,617,013 A | | 10/1986 | Betz |
| 4,634,420 A | | 1/1987 | Spinosa et al. |
| 4,788,729 A | * | 12/1988 | Walker .................. 5/711 |
| 4,857,047 A | | 8/1989 | Amoils |
| 5,255,675 A | | 10/1993 | Kolobow |
| 5,263,934 A | | 11/1993 | Haak |
| 5,269,296 A | | 12/1993 | Landis |
| D358,475 S | | 5/1995 | Choksi et al. |
| 5,477,852 A | | 12/1995 | Landis et al. |
| 5,575,774 A | | 11/1996 | Chen |
| 5,626,565 A | | 5/1997 | Landis et al. |
| 5,687,715 A | | 11/1997 | Landis et al. |
| 5,730,727 A | | 3/1998 | Russo |
| D410,021 S | | 5/1999 | Heyman et al. |
| 5,899,878 A | | 5/1999 | Glassman |
| 6,041,777 A | | 3/2000 | Faithfull et al. |
| 6,045,516 A | | 4/2000 | Phelan |
| 6,050,263 A | | 4/2000 | Choksi et al. |
| 6,149,622 A | | 11/2000 | Marie |
| D439,973 S | | 4/2001 | Choksi |
| D449,378 S | | 10/2001 | Rogone et al. |
| 6,494,203 B1 | | 12/2002 | Palmer |
| 6,520,021 B1 | | 2/2003 | Wixey et al. |
| D474,269 S | | 5/2003 | Choksi et al. |
| 6,770,050 B2 | | 8/2004 | Epstein |
| 6,795,722 B2 | | 9/2004 | Sheraton et al. |
| 6,805,120 B1 | | 10/2004 | Jeffrey et al. |
| 6,805,129 B1 | | 10/2004 | Pless et al. |
| D506,547 S | | 6/2005 | Cruz et al. |
| 6,958,050 B1 | | 10/2005 | Choski et al. |
| 7,066,917 B2 | | 6/2006 | Talamonti |
| 7,077,154 B2 | | 7/2006 | Jacobs et al. |
| 7,185,681 B2 | | 3/2007 | Romano |
| D590,056 S | | 4/2009 | McCrary et al. |
| 7,601,001 B1 | | 10/2009 | McCrary et al. |
| 2001/0044599 A1 | | 11/2001 | Lo |
| 2002/0108614 A1 | | 8/2002 | Schultz |
| 2003/0047185 A1 | | 3/2003 | Olsen et al. |
| 2003/0065263 A1 | | 4/2003 | Hare et al. |
| 2003/0069553 A1 | | 4/2003 | Talamonti |
| 2004/0065330 A1 | | 4/2004 | Landis |
| 2004/0244804 A1 | | 12/2004 | Olsen et al. |
| 2005/0049547 A1 | | 3/2005 | Anspach et al. |
| 2005/0072470 A1 | | 4/2005 | Jacobs et al. |
| 2005/0150505 A1 | | 7/2005 | Burrow et al. |
| 2005/0182353 A1 | | 8/2005 | Schmidberger et al. |
| 2005/0256462 A1 | | 11/2005 | Underwood |
| 2005/0277898 A1 | | 12/2005 | Dimalanta et al. |
| 2006/0079832 A1 | | 4/2006 | Akahoshi |
| 2006/0229632 A1 | | 10/2006 | Madden et al. |
| 2007/0078378 A1 | | 4/2007 | Kao et al. |
| 2007/0107737 A1 | | 5/2007 | Landis et al. |
| 2007/0175473 A1 | | 8/2007 | Lewis et al. |
| 2007/0191783 A1 | | 8/2007 | Shaw et al. |
| 2008/0216830 A1 | * | 9/2008 | Richards et al. ......... 128/204.18 |

FOREIGN PATENT DOCUMENTS

| | | |
|---|---|---|
| WO | 98/58694 A | 12/1998 |
| WO | 01/64272 A | 9/2001 |
| WO | 2004/033007 A1 | 4/2004 |
| WO | 2009/029702 A1 | 3/2009 |

OTHER PUBLICATIONS

International Search Report mailed Nov. 2, 2004 for International Application No. PCT/IB2003/04419, 2 pages.
OA dated Jan. 13, 2013 for U.S. Appl. No. 11849268, 34 pages.
Written Opinion of the International Searching Authority mailed Nov. 6, 2008 for PCT Application No. PCT/US2008/074574, 35 pages.
OA dated Apr. 6, 2009 for U.S. Appl. No. 11849268, 9 pages.
International Search Report mailed Nov. 6, 2008 for International Application No. PCT/US2008/074748, 2 pages.
International Search Report mailed Nov. 6, 2008 for International Application No. PCT/US2008/074574, 2 pages.
Fisher & Paykel Healthcare Product Catalog copyright 2004, 16 pages.
Fisher & Paykel Healthcare Annual Report 2002, 32 pages.
Petry, Fisher & Paykel 510(k) Summary of Safety and Effectiveness Information, 6 pages, Apr. 3, 2003.
http://www.fphcare.com/rsc.html, last accessed Apr. 26, 2010, 1 page.
http://www.fphcare.com/rsc/infant-care/resuscitation.html, last accessed Apr. 26, 2010, 1 page.
http://www.fphcare.com/rsc/infant-care/non-invasive-ventilation.html, last accessed Apr. 26, 2010, 1 page.
http://www.fphcare.com/rsc/rac-clinical-and-applications/infant-c-a/why-bubble-cpap-is-vital.html, last accessed Apr. 26, 2010, 2 pages.
http://www.fphcare.com/product-overview/chambers/humidification-chambers/mr290-autofeed.html, last accessed Apr. 26, 2010, 1 page.
http://www.fphcare.com/product-overview/chambers/humidification-chambers/mr210-mr250-chamber.html, last accessed Apr. 26, 2010, 1 page.
http://www.fphcare.com/product-overview/chambers/humidification-chambers/mr225-manual-feed.html, last accessed Apr. 26, 2010, 1 page.
http://www.fphcare.com/osa/cpap-solutions/cpap/sleepstyle-200.html, last accessed Apr. 26, 2010, 2 pages.
http://www.fphcare.com/osa/cpap-solutions/cpap/sleepstyle-240.html, last accessed Apr. 26, 2010, 2 pages.
http://www.fphcare.com/osa/cpap-solutions/cpap/sleepstyle-600.html, last accessed Apr. 26, 2010, 2 pages.
http://www.fphcare.com/osa/cpap-solutions/autocpap/sleepstyle-250.html, last accessed Apr. 26, 2010, 2 pages.
Babi.Plus™ Bubble PAP Valve 0—10 cm H20, Safe, accurate method to deliver CPAP therapy in neonatal critical care environments, 2010, 1 page.
B&B Medical Technologies, Babi.Plus™ Bubble PAP Valve 0—10 cm H2O, 2005, 2 pages.
B&B Medical Technologies, Babi.Plus™ Bubble PAP Valve 0—10 cm H2O gives clinicians a safe, accurate, convenient method to deliver CPAP therapy for neonates and premature infants, 1 page, Mar. 19, 2010.
Airways Development LLC, Waterseal Canister & Accessories, Aug. 2004, 1 page.
A Plus Medical 510(k) Summary, 5 pages, May 20, 2009.
Presentation Jul. 2007, 16 pages.
http://www.airwaysdevelopment.com/product.asp, last accessed Apr. 28, 2010, 1 page.
Frischer, et al. Eosinophil-derived proteins in nasal lavage fluid of neonates of allergic parents and the development of respiratory symptoms during the first 6 months of life. Allergy 2000: 55: 773-777, ISSN 0105-4538. http://onlinelibrary.wiley.com/doi/10.1034/j.1398-9995.2000.00773.x/pdf. Last accessed Oct. 6, 2010, 5 pages.
Waisman. Non-Traumatic Nasopharyngeal Suction in Premature Newborn Infants with Upper Airway Obstruction from Secretions Following Nasal CPAP. J Pediatr 2006;149:279. http://download.journals.elsevierhealth.com/pdfs/journals/0022-3476/PIIS002234760600148X.pdf. Last accessed Oct. 6, 2010, 1 page.
Okada, et al. Pressure-Controlled Dual Irrigation-Suction System for Microneurosurgery: Technical Note. www.neurosurgery-online.com, E625, vol. 65, No. 3, Sep. 2009. http://pt.wkhealth.com/pt/re/merck/pdfhandler.00006123-200909000-00032.pdf;

(56) References Cited

OTHER PUBLICATIONS jsessionid=MsvLyq9Y7c928drTcGsSkYzDJy61CfX4zby C66q6kcxL5GhdRLKy!1137524313!181195628!8091!-1. Last accessed Oct. 6, 2010, 4 pages.

Vain, et al. Oropharyngeal and nasopharyngeal suctioning of meconium-stained neonates before delivery of their shoulders: multicenter, randomized controlled trial (Abstract), The American College of Obstetricians and Gynecologists, vol. 104, No. 5, Part 1, Nov. 2004.

Garzon, et al. Management of Respiratory Syncytial Virus With Lower Respiratory Tract Infection in Infants and Children. AACN Clinical Issues, vol. 13, No. 3, Aug. 2002, pp. 421-430.

Balfour-Lynn, et al. Nasal IgA response in wheezy infants. Archives of Disease in Childhood 1993; 68: 472-476. Last accessed Oct. 18, 2010, 5 pages.

Celik, et al. A Current Conflict: Use of Isotonic Sodium Chloride Solution on Endotracheal Suctioning in Critically Ill Patients. Dimens Crit Care Nurs. 2006;25(1):11/14. http://www.nursingcenter.com/pdf.asp?AID=630764. Last accessed Oct. 18, 2010, 4 pages.

Stokowski (Section Editor). Endotracheal Suctioning Increases Cerebral Blood Flow in the Very Low Birth-Weight Infant, Advances in Neonatal Care: Apr. 2008—vol. 8—Issue 2—pp. 75-77. doi: 10.1097/01. ANC.0000317254.30460.5d, Noteworthy Professional News, downloaded Mar. 24, 2008, 3 pages.

Virolainen, et al. New Method to Assess Dilution of Secretions for Immunological and Microbiological Assays. Journal of Clinical Microbiology, May 1993, p. 1382-1384, vol. 31, No. 5. http://jcm.asm.org/cgi/reprint/31/5/1382. Last accessed Oct. 19, 2010, 3 pages.

Heikkinen, et al. Quantification of Cytokines and Inflammatory Mediators in Samples of Nasopharyngeal Secretions with Unknown Dilution. Pediatric Research: Feb. 1999—vol. 45—Issue 2—pp. 230-234. http://journals.lww.com/pedresearch/Fulltext/1999/02000/Quantification_of_Cytokines_and_Inflammatory.12.aspx#. Last accessed Oct. 19, 2010, 9 pages.

Foglia, et al. Ventilator-Associated Pneumonia in Neonatal and Pediatric Intensive Care Unit Patients. Clinical Microbiology Reviews, vol. 20, No. 3, Jul. 2007, p. 409-425. http://cmr.asm.org/cgi/reprint/20/3/409.pdf. Last accessed Oct. 19, 2010, 17 pages.

Kaiser, et al. Tracheal suctioning is associated with prolonged disturbances of cerebral hemodynamics in very low birth weight infants. Journal of Perinatology (2008) 28, 34-41, published online, Oct. 25, 2007. http://www.umanitoba.ca/faculties/medicine/units/pediatrics/sections/neonatology/media/Oct20-08.pdf. Last accessed Oct. 19, 2010, 8 pages.

Folk. Guide to Capillary Heelstick Blood Sampling in Infants. Advances in Neonatal Care . . . vol. 7, No. 4 . . . pp. 171-178. http://www.nursingcenter.com/pdf.asp?AID=735611. Last accessed Oct. 19, 2010, 8 pages.

Lasocki, et al. Open and Closed-circuit Endotracheal Suctioning in Acute Lung Injury: Efficiency and Effects on Gas Exchange. Anesthesiology: Jan. 2006—vol. 104—Issue 1—pp. 39-47, Clinical Investigations. http://journals.lww.com/anesthesiology/Fulltext/2006/01000/Open_and_Closed_circuit_Endotracheal_Suctioning_in.8.aspx. Last accessed Oct. 19, 2010, 9 pages.

Lanter. Clinical Research and the Development of New Devices: Considerations for Nurses. Dimensions of Critical Care Nursing: May/Jun. 2007—vol. 26—Issue 3—pp. 117-120. http://journals.lww.com/dccnjournal/Fulltext/2007/05000/Clinical_Research_and_the_Development_of_New.7.aspx. Last accessed Oct. 19, 2010, 4 pages.

National Nosocomial Infections Surveillance (NNIS) System Report, data summary from Jan. 1992 through Jun. 2004, issued Oct. 2004. http://www.cdc.gov/ncidod/dhqp/pdf/nnis/2004NNISreport.pdf. Last accessed Oct. 19, 2010, 16 pages.

Ingram, et al. *Eosinophil Cationic Protein* in Serum and Nasal Washes from Wheezing Infants and Children. Journal of Pediatrics, vol. 127, issue 4, Oct. 1995. Retrieved from the internet on Nov. 10, 2010, 11 pages.

Heikkenen, et al. Free Secretory Component as a Standardization Protein for Nasopharyngeal Specimens from Children with Upper Upper Respiratory Tract Infection. Acta Paediatr 88: 150-153, 1999.

Bonner, et al. The Nursing Care of the Infant Receiving Bubble CPAP Therapy. Advances in Neonatal Care . . . vol. 8, No. 2 . . . pp. 78-95. Last accessed Nov. 13, 2010, 18 pages.

Klimek, et al. Norm Values for Eosinophil Cationic Protein in Nasal Secretions: Influence of Specimen Collection. Clinical and Experimental Allergy, 1999, vol. 29, pp. 367-374.

Norris, et al. Nursing Procedures and Alterations in Transcutaneous Oxygen Tension in Premature Infants. Nursing Research, vol. 31, No. 6, Nov./Dec. 1982, pp. 330-336.

Samolinski, et al. Changes in Nasal Cavity Dimensions in Children and Adults by Gender and Age. Laryngoscope, 117:1429-1433, Aug. 2007, The American Laryngological, Rhinological and Otological Society, Inc.

Weinstein, et al. Recommendations of the Panel on Cost-Effectiveness in Health and Medicine. JAMA, Oct. 16, 1996—vol. 276, No. 15, 6 pages.

OA dated May 28, 2010 for U.S. Appl. No. 11849268, 39 pages.

* cited by examiner

PRESSURE RELEASE SYSTEMS, APPARATUS AND METHODS

CROSS-REFERENCE TO RELATED APPLICATIONS

This application claims the benefit of U.S. Provisional Patent Application Ser. No. 61/149,875 titled "PRESSURE RELEASE SYSTEMS AND APPARATUS," which was filed Feb. 4, 2009 and the entire contents of which are incorporated herein by reference.

BACKGROUND

I. Field

The present invention relates to pressure release systems and apparatus, in general, and pressure release systems and apparatus for respiratory circuits, in particular.

II. Background

Respiratory circuits are typically employed to transport a gas to or from the respiratory system of a patient. In some cases, due to machine malfunction, kinking of tubing in the respiratory circuit and/or error by the healthcare professional, the patient can be provided a gas at a pressure that is too high. Excessive pressures can endanger the respiratory systems of patients, potentially causing lung ruptures and other serious medical conditions.

Additionally, in many cases, healthcare professionals provide care to more than one patient during a work shift. Accordingly, the healthcare professional cannot be aware of the pressure experienced by a patient at any particular instant of time. Therefore, a gas of an excessive pressure can be provided to the patient for an unacceptable period of time before the problem is noticed and addressed by the professional.

Accordingly, there is a desire for systems and apparatus that detect and relieve excessive pressure in respiratory circuits, and provide an audible alert of the excessive pressure in the respiratory circuits.

Typically pressure detection apparatus are large and heavy weight and therefore provided on a support base with humidifiers, temperature gauges, gas blenders, gas sources and other components for providing gas to and monitoring of a patient, as opposed to being provided inline in the circuit and close to the patient. In typical embodiments, the respiratory circuit, from the location of the pressure detection device to the patient and/or the length of the tubing coupling the pressure detection device to the patient, can be four to five feet long. Accordingly, the systems often do not provide accurate pressure detection near the patient, resulting in a high likelihood of undetected overpressure at the patient and/or are of such a large size that the conventional systems pose a danger of snagging a patient or healthcare professional or the fabric or clothing of the patient or healthcare professional.

Accordingly, there is a desire for lightweight, small systems and apparatus that detect and relieve excessive pressure in respiratory circuits, provide an audible alert of the excessive pressure in the respiratory circuits and/or are placed inline in the respiratory circuit at a location that is proximal to the patient.

SUMMARY

In one embodiment, a respiratory circuit is provided. The respiratory circuit can include: an adapter having a plurality of connectors of two or more different internal or outer diameters; and a pressure release valve configured to emanate sound if a pressure of a gas received at the pressure release valve is greater than or equal to an activation pressure of the pressure release valve, the pressure release valve also being formed with a body portion configured and having a first end of the body portion coupled to one of the plurality of connectors of the adapter, wherein the pressure release valve is coupled inline in the respiratory circuit via the adapter and in close proximity to a patient location.

In another embodiment, a respiratory circuit apparatus is provided. The respiratory circuit apparatus can include: a pressure release valve configured to emanate sound if a pressure of a gas received at the pressure release valve is greater than or equal to an activation pressure of the pressure release valve, the pressure release valve also being formed with a body portion configured and having a first end of the body portion coupleable to one of a plurality of connectors of an adapter configured to be positioned inline in a respiratory circuit.

In another embodiment, a respiratory circuit pressure release system is provided. The respiratory circuit pressure release system can include: a respiratory circuit adaptable pressure release valve configured with at least one port dimensioned to be coupled to an adapter having a plurality of adapter ports for coupling the adapter and one or more mounted devices to the respiratory circuit, wherein the respiratory circuit adaptable pressure release valve is coupleable in series in the respiratory circuit via the adapter, and wherein the respiratory circuit adaptable pressure release valve is configured to whistle if a pressure of a gas received at the respiratory circuit adaptable pressure release valve is greater than or equal to an activation pressure of the respiratory circuit adaptable pressure release valve.

BRIEF DESCRIPTION OF THE DRAWINGS

Purposes and scope of the exemplary embodiments described below will be apparent from the following detailed description in conjunction with the appended figures in which like reference characters are used to indicate like elements, and in which.

DETAILED DESCRIPTION

It is noted that in the figures, the illustration of components as separate entities from one another is merely exemplary. The components can be combined, integrally formed, separated and/or duplicated to support various functions. As used herein, the term "integrally formed" shall mean, continuous in form such that the component is a single, molded body (as compared to multiple components coupled together). Additionally, the figures depict simplified views and can include alternative components that are not depicted but which remain within the spirit of the embodiments of the invention described herein.

Figure 3A:
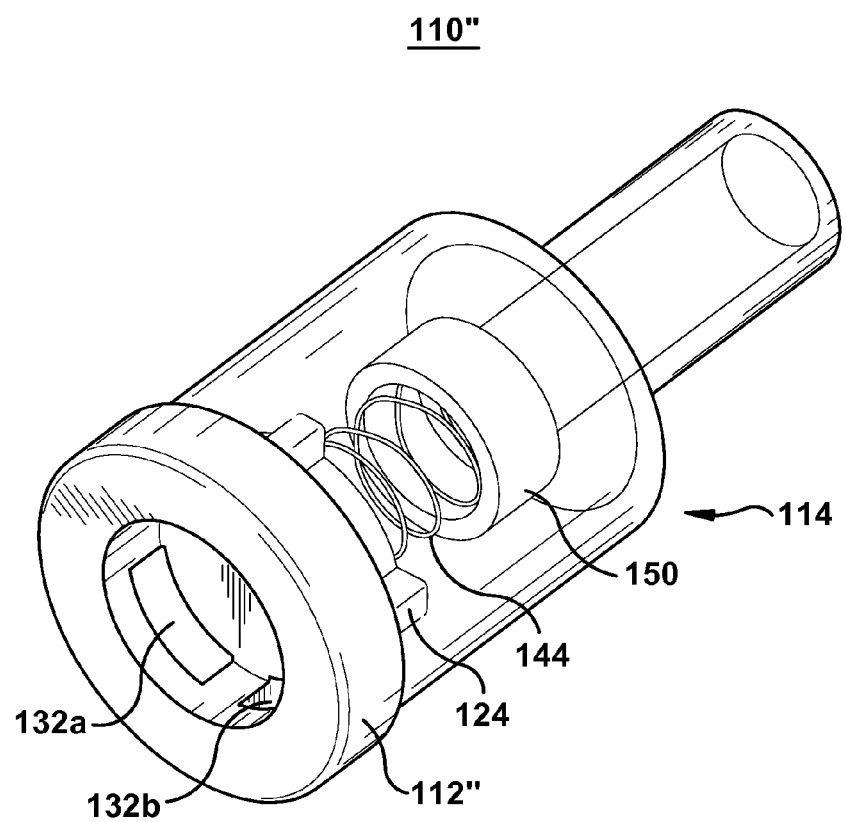
FIGS. 3A and 3B are views of unmarked pressure release valves according to embodiments of the present invention.
Figure 3B:
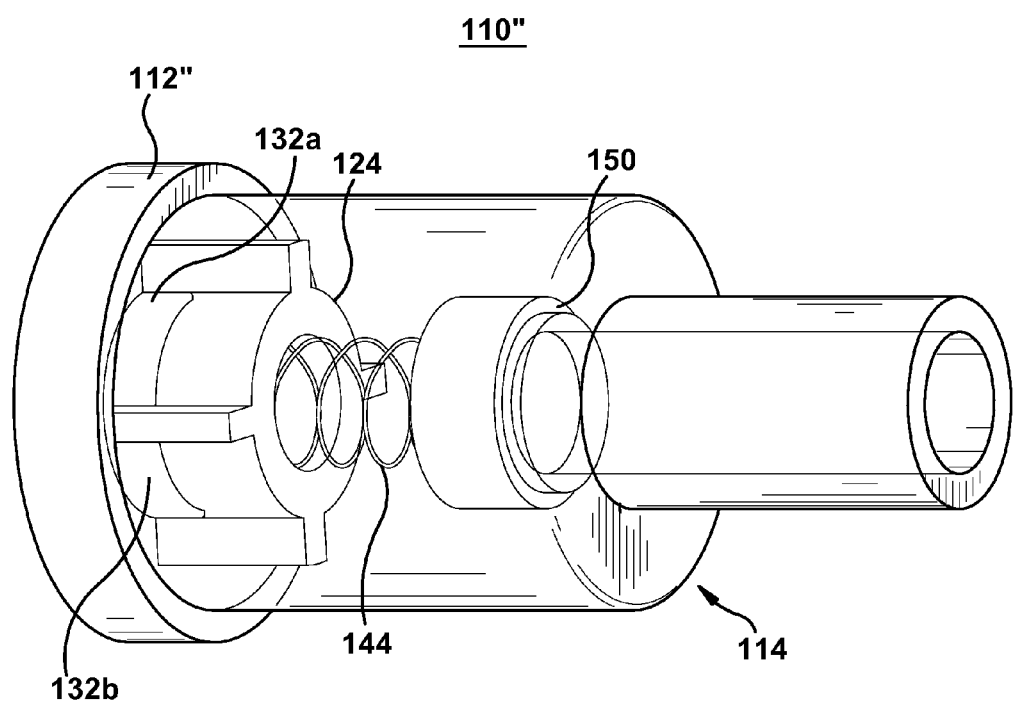
Figure 4A:
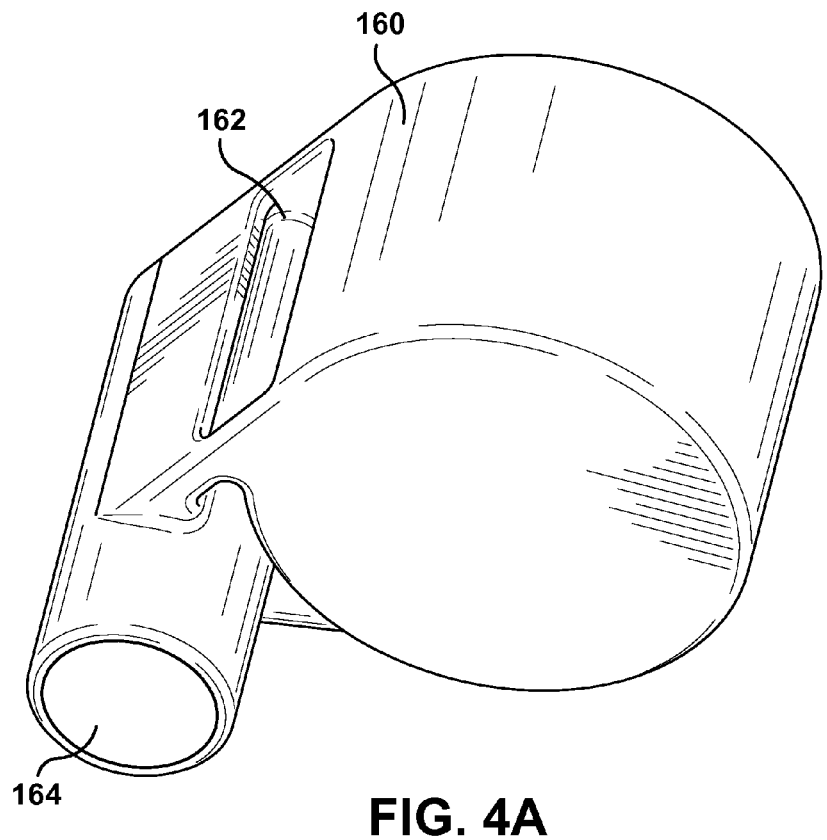
FIGS. 4A, 4B and 4C are views of an audible apparatus according to embodiments of the present invention.
Figure 4B:
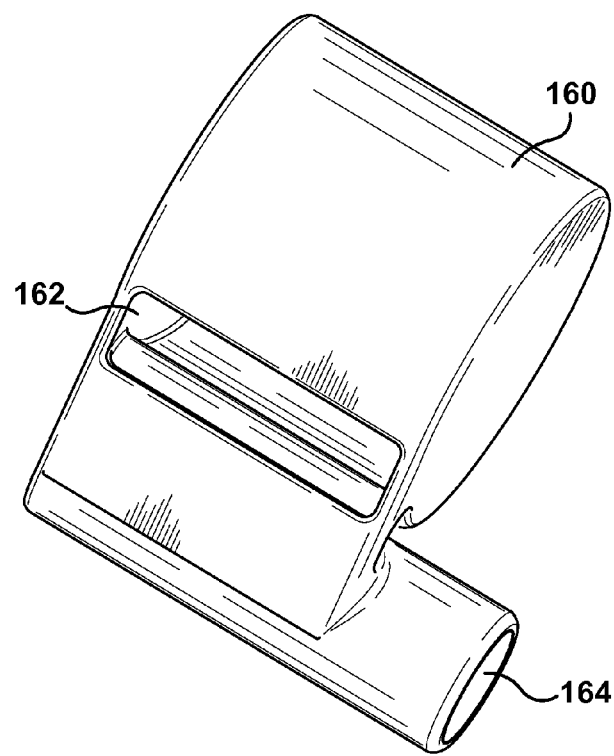
Figure 4C:
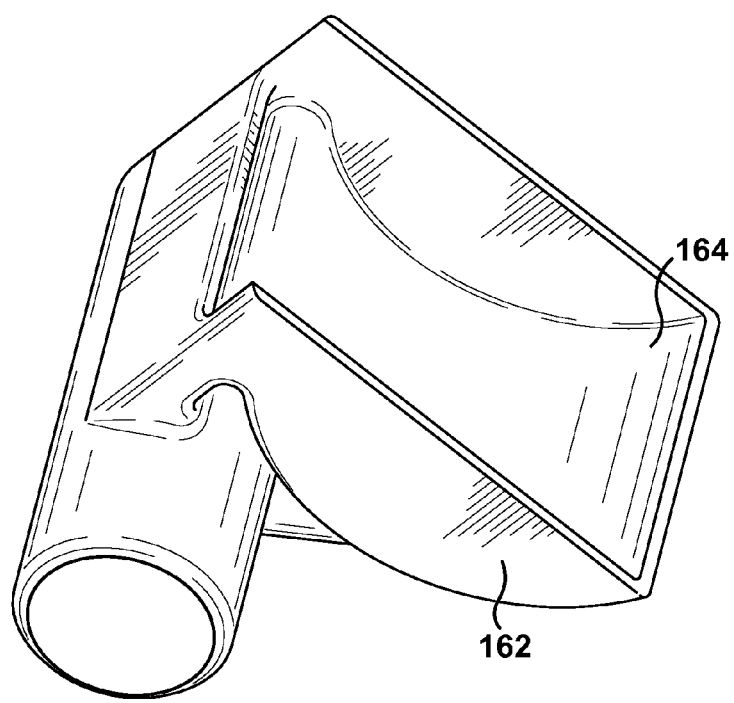
Figure 5A:
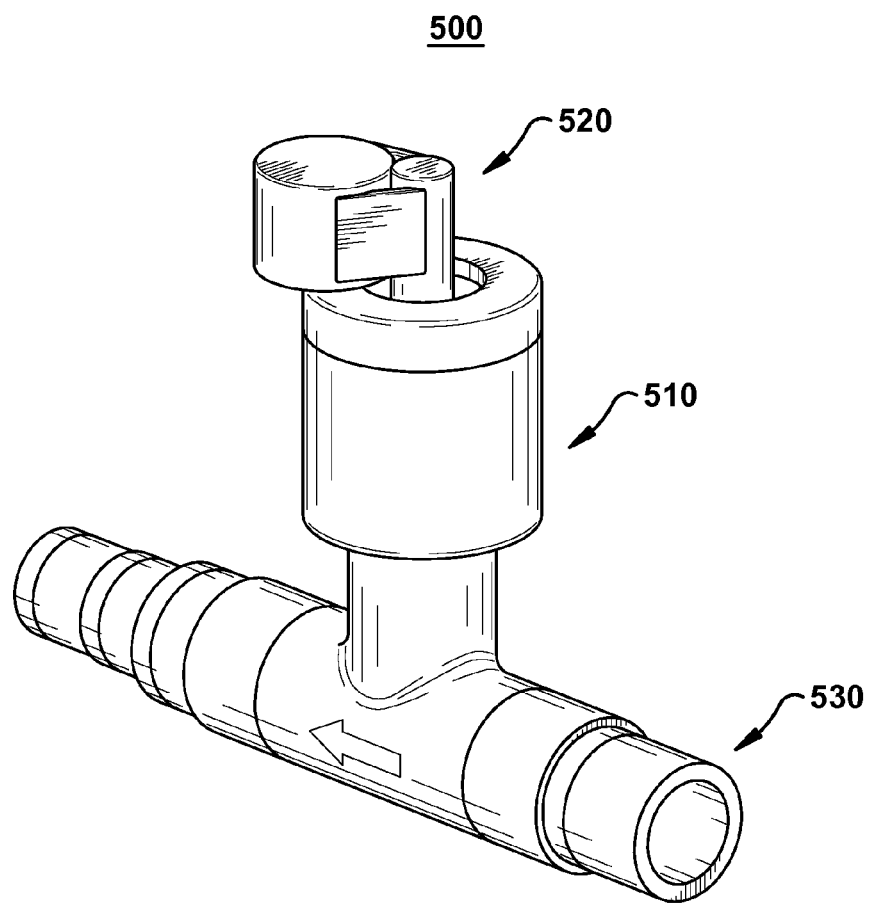
FIGS. 5A, 5B, 5C and 5D are views of a pressure release system according to embodiments of the present invention.
Figure 5B:
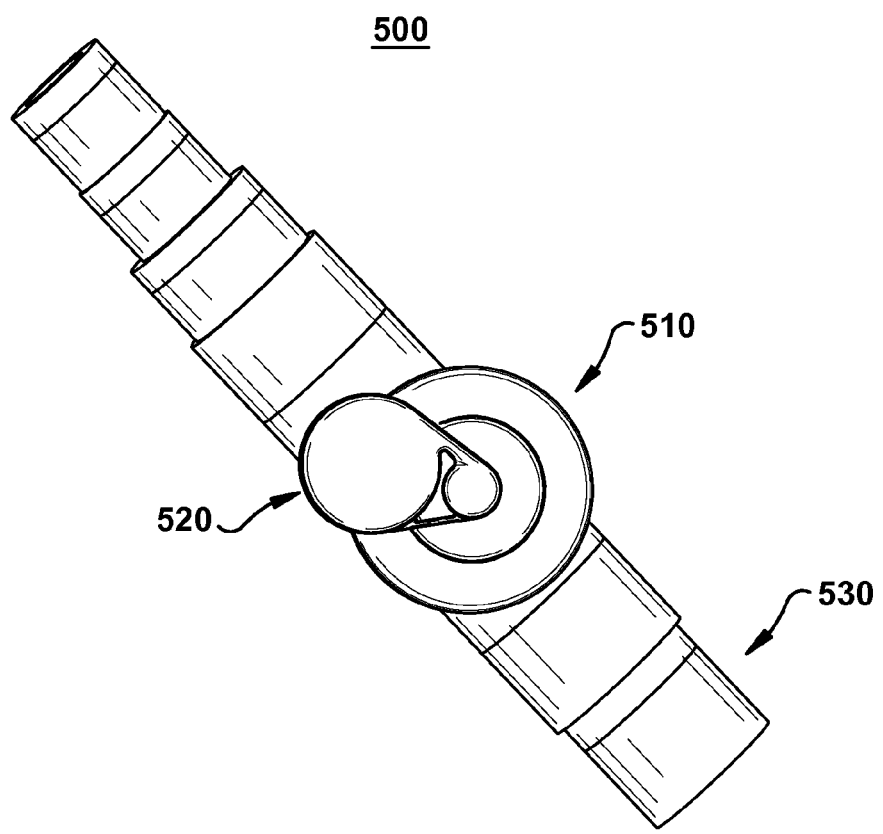
Figure 5C:
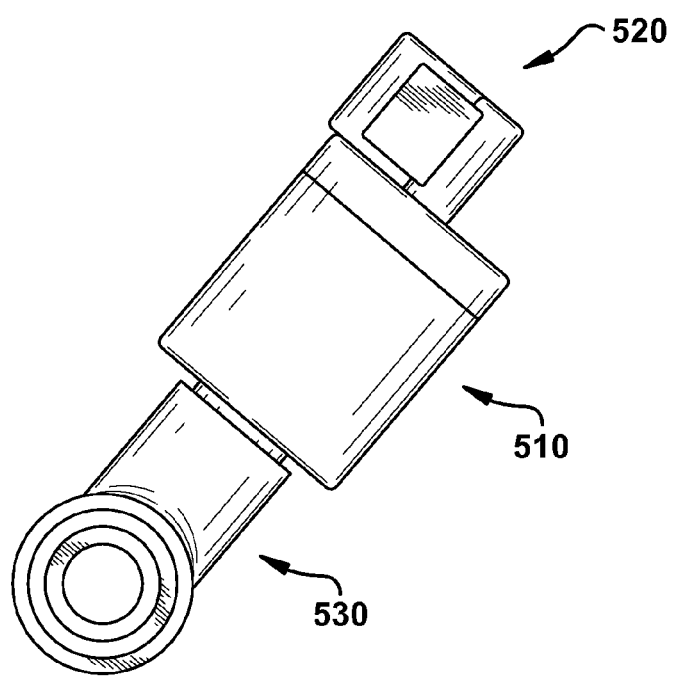
Figure 5D:
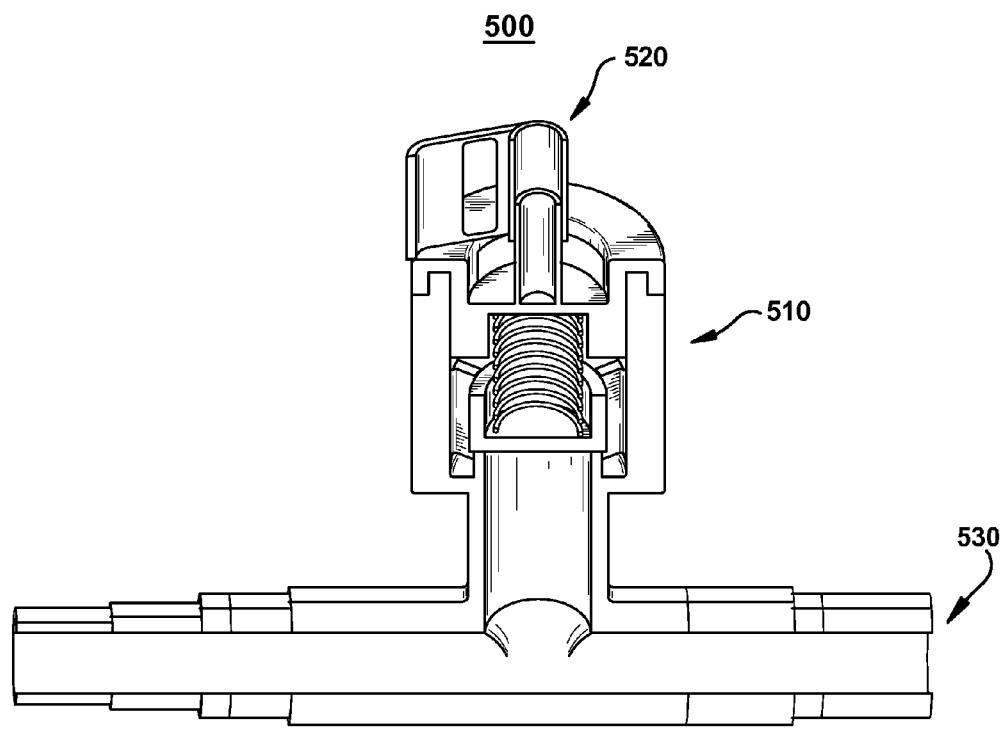

FIGS. 1A, 1B, 1C, 1D, 1E, 1F and 1G are views of pressure release systems according to embodiments of the present invention. FIGS. 2A, 2B, 2C and 2D are views of pressure release systems according to embodiments of the present invention. FIGS. 3A and 3B are views of unmarked pressure release valves according to embodiments of the present invention. FIGS. 4A, 4B and 4C are views of an audible apparatus according to embodiments of the present invention.

Embodiments of the pressure release systems 100, 100', the pressure release valves 110, 110', 110", 110''' and/or the audible apparatus 158, 158', as shown in FIGS. 1A, 1B, 1C, 1D, 1E, 1F, 1G, 2A, 2B, 2C, 2D, 3A, 3B, 4A, 4B and/or 4C, will now be described.

The pressure release systems 100, 100' can include a pressure release valve 110, 110', 110", 110''' and an audible apparatus 158, 158'. In some embodiments, the audible apparatus 158, 158' can be an apparatus capable of generating a sound that is audible to humans less than one year old to 70 years old. In some embodiments, the audible apparatus 158, 158' can be an apparatus capable of generating a sound that is between 40 and 50 decibels, between 40 and 60 decibels, between 40 and 80 decibels, or at least 40 decibels.

The pressure release valve 110, 110', 110", 110''' can be coupled to or integrally formed with the audible apparatus 158 such that the pressure release valve 110, 110', 110", 110''' is in fluid communication with the audible apparatus 158, 158'. In various embodiments, the pressure release valve 110, 110', 110", 110''' can be a spring-loaded valve or the pressure release valve 110, 110', 110", 110''' can be a fixed pressure valve, which does not require adjustment of the activation pressure.

In various embodiments, the fixed pressure embodiment can provide a structure that enables the gas to flow into the inner chamber immediately and at a pressure suitable for activating the audible apparatus immediately, or substantially at the time that the gas pressure is initially detected as being greater than or equal to the activation pressure (or the activation pressure+/−5-15% of the activation pressure).

In some embodiments, the fixed pressure valve can be configured as the pressure release valve described herein but can include a magnet inside of the inner chamber instead of the compression spring. The magnet can be disposed to apply a magnetic force on the interior cap maintaining the interior cap in a position to block gas from flowing into the inner chamber. When the pressure of the gas is greater than or equal to the activation pressure (or the activation pressure+/−5-15% of the activation pressure), the pressure overcomes the magnetic force, and the magnet can be forced in an upward position away from the interior cap, thereby causing the pressure release valve to open completely and substantially immediately upon detection. In this way, the gas pressure detection and the emanation of the sound from the audible apparatus (and alerting the healthcare professional can be substantially real-time) in some embodiments.

The activation pressure can be the gas pressure value (+/− a 5-15% margin of error) that, when exceeded or when the gas pressure is equal to such pressure, the pressure release valve 110, 110', 110", 110''' can open (and thereby emit gas in the pressure release valve 110, 110', 110", 110''' to the audible apparatus 158, 158').

As indicated above, in various embodiments, the activation pressure can be any value in a range of pressure values. The range of pressure values can be those that are within a range of values that are +/−5-15% of the activation pressure that the pressure release valve 110, 110', 110", 110''' is designed to have. Accordingly, for a selected activation pressure, a margin of error can exist whereby other pressures that are +/−5-15% of the activation pressure can also cause the pressure release valve 110, 110', 110", 110''' to open.

In some embodiments, the margin of error can be a function of two measurements of the pressure at which a pressure release valve 110, 110', 110", 110''' opens at two different flow rates of the gas that the pressure release valves 110, 110', 110", 110''' detects. The margin of error can be calculated by measuring the actual pressure at which the pressure release valve 110, 110', 110", 110''' opens for gas provided at 8 liters per minute (lpm) and at 15 lpm. For a pressure release valve 110, 110', 110", 110''' designed to have an activation pressure of 20 cm $H_2O$, at 8 lpm, the pressure release valve 110, 110', 110", 110''' can open at 17 cm $H_2O$ and at 15 lpm, the pressure release valve 110, 110', 110", 110''' can open at 24 cm $H_2O$. Because the pressure release valve has an activation pressure of 20 cm $H_2O$, but it can activate at a value as low as 17 cm $H_2O$ or as high as 24 cm $H_2O$, the margin of error can be 5-15% of the activation pressure, and the activation pressure can actually be 20 cm $H_2O$. As such, the pressure release valve can activate at pressures that are greater than or equal to the activation pressure (or, in some embodiments, activate at a pressure that is greater than or equal to the activation pressure+a margin of error that is +/−5-15% of the activation pressure). In general, in various embodiments, the margin of error that can be considered when determining the pressure at which a pressure release valve will activate, can be a function of a first pressure at which the pressure release valve opens upon receiving a gas at a typical minimum flow rate, and a second pressure at which the pressure release valve opens upon receiving a gas at a typical maximum flow rate. The typical minimum and maximum flow rates can differ due to any number of factors including, but not limited to, the type of the respiratory care and/or the gas source of the respiratory circuit. In some embodiments, the flow rate for the pressure release system can be a value between 1 to 15 lpm.

The pressure release valve 110, 110', 110", 110''' can relieve internal pressure within a respiratory circuit of a pressure system within the pressure release valve pressure range. Thus, the pressure release valve can be used to regulate the maximum pressure achievable within a pressure system.

In various embodiments, the pressure release valve 110, 110', 110", 110''' can have an activation pressure of 20, 40 or 60 cm $H_2O$. In embodiments wherein the activation pressure is 40 cm $H_2O$, the pressure release valve 110, 110', 110", 110''' can be adapted to close and/or remain closed when the pressure of a gas detected in the pressure release valve 110, 110', 110", 110''' is less than 35-40 cm $H_2O$. In some embodiments, the 40 cm $H_2O$ pressure can correspond to an 8 lpm flow rate. In some embodiments, the pressure release valve can block airflow passage at pressures under 35-40 cm $H_2O$ when the pressure release valve has an activation pressure of 40 cm $H_2O$. In embodiments wherein a very large pressure, such as 60 cm $H_2O$, is detected, the pressure release valve 110, 110', 110", 110''' can be open and/or remain open until the pressure is reduced to a value less than the activation pressure. In some embodiments, 60 cm $H_2O$ can be considered a maximum pressure for the circuit. In other embodiments, 80 cm $H_2O$ can be considered the maximum pressure. In any case, in embodiments wherein the pressure of the gas equals or is greater than 60 cm $H_2O$ (or 60 cm $H_2O$+a margin of error that is +/−5-15% of 60 cm $H_2O$, or the maximum pressure), the pressure release valve 110, 110', 110", 110''' can be open and/or remain open until the pressure is reduced to a value less than the activation pressure. In various embodiments, the pressure release valve

110, 110', 110", 110'" can be configured to activate at any number of pressures within a range from 5 cm $H_2O$ to 80 cm $H_2O$ (or 5 cm $H_2O$ to 80 cm $H_2O$+a margin of error that is +/−5-15% of 5 cm $H_2O$ or 80 cm $H_2O$, respectively).

In some embodiments, the pressure release valve 110, 110', 110", 110'" is disposable and/or composed of disposable materials. As such, the pressure release valve 110, 110', 110", 110'" can be composed of materials that are not autoclavable in some embodiments. In some embodiments, the pressure release valve 110, 110', 110", 110'" can be composed of non-flammable materials. In some embodiments, the pressure release valve 110, 110', 110", 110'" can also be supplied sterile.

In some embodiments, the pressure release valve 110, 110', 110", 110'" can be solely mechanical and require no electrical components for operation. As such, the cost of the pressure release valve 110, 110', 110", 110'" can be much lower than valves that involve electronic equipment. In some embodiments, the edges of each of the components of the pressure release valve 110, 110', 110", 110'" can have at least 0.005 inch diameter edge breaks to reduce the instances of sharp edges that may injure a patient or healthcare professional. The pressure release valve 110, 110', 110", 110'" can be configured to be able to couple to the pressure release system 100, 100' without supports that are external to the pressure release valve 110, 110', 110", 110'".

In some embodiments, the pressure release valve 110, 110', 110", 110'" (or the pressure release system 710, 710' discussed below with reference to FIG. 7) can be approximately 1 inch in height. In other embodiments, the pressure release valve 110, 110', 110", 110'" (or the pressure release system 710, 710' discussed below with reference to FIG. 7) can be less than 1 inch in height. In some embodiments, the pressure release valve 110, 110', 110", 110'" (or the pressure release system 710, 710' discussed below with reference to FIG. 7) can be 25-30% of the height of the conventional valves and systems, which can be several inches in height.

In some embodiments, the pressure release valve 110, 110', 110", 110'" (or the pressure release system 710, 710' discussed below with reference to FIG. 7) can be lightweight (e.g., 10 grams and/or approximately 20-25% of the weight of the conventional valves or systems, which can be 40-50 grams) so as to reduce the amount of stress on the respiratory circuit relative to models of valves that may not be lightweight.

In some embodiments, the pressure release valve 110, 110', 110", 110'" can be a one-way valve that enables gas to flow to a patient while opening and thereby venting gas to the atmosphere when excessive gas pressures are received at the pressure release valve 110, 110', 110", 110'".

In one embodiment, the pressure release valve 110, 110', 110", 110'" can be a single patient use medical device that has an activation pressure of 40 cm $H_2O$. The pressure release valve 110, 110', 110", 110'" can be configured to provide an audible alert via a whistle tone when the activation level is reached and the pressure release valve opens. In some embodiments, the cap 112, 112', 112" of the pressure release valve can be color coded to indicate the activation pressure of the pressure release valve. In some embodiments, the cap 112, 112', 112" can include information indicative of the activation pressure. The information can be molded into the cap and/or applied to the cap by any suitable methods including, but not limited to, applying the information to a label and adhering the label to the cap 112, 112', 112".

In some embodiments, the pressure release system 100, 100' can receive a gas having a pressure. The pressure release system 100, 100' can detect whether the pressure is greater than or equal to the activation pressure (or, in some embodiments, activate at a pressure that is greater than or equal to the activation pressure+a margin of error that is +/−5-15% of the activation pressure).

If the pressure is greater than or equal to the activation pressure (or, in some embodiments, greater than or equal to the activation pressure+a margin of error that is +/−5-15% of the activation pressure), the pressure release valve 110, 110', 110", 110'" can open, thereby emitting a volume of the gas to the audible apparatus 158, 158'. The audible apparatus 158, 158' can receive the emitted gas and generate a sound when the gas received by the audible apparatus 158, 158' is emitted to the atmosphere from the audible apparatus 158, 158'.

If the pressure is less than the activation pressure, the pressure release valve 110, 110', 110", 110'" can close (or remain closed) and the gas can be provided to the patient. The patient can be any type of living being to which a gas can be provided to or from during respiratory care. By way of example, but not limitation, the patient can be a human, animal, neonate, infant, pediatric, adult and/or geriatric patient. As such, the pressure release valve can regulate airway pressure provided to pediatric, infant and/or neonate patients. In some embodiments, the pressure release valve can regulate airway pressure provided to adult, geriatric patients. In some embodiments, the pressure release valve can regulate airway pressure provided to humans, plants and/or animals. In some embodiments, the patient can be a plant to which oxygen or other gas can be provided. In various embodiments, the respiratory care can be any type of respiratory care wherein a gas is provided to and/or from a patient through the use of a respiratory circuit. In various embodiments, the respiratory care can include any care provided via continuous positive airway pressure respiratory circuits, high flow respiratory circuits, bi-level respiratory circuits, end/expiratory positive airway pressure respiratory circuits and/or inspiratory positive airway pressure respiratory circuits and/or methodologies. In some embodiments, the circuits could be, but are not limited to being, Bubble Nasal Continuous Positive Airway Pressure (BNCPAP) circuits, High/Heated Flow Nasal Cannula (HFNC) circuits or any other kind of patient breathing circuit in which gas is provided to the patient.

Providing pressure release valves 110, 110', 110", 110'" having different activation pressures can provide the healthcare professional the flexibility to select the best possible pressure release valve to regulate the pressure provided to the patient. Healthcare professionals can include, but are not limited to, physicians, nurses, respiratory therapists or any other healthcare professional that provides respiratory care to patients.

The components of various embodiments of the pressure release valve 110, 110', 110", 110'" will now be described in detail. The pressure release valve 110, 110', 110", 110' can include a body 114, 114' and a cap 112, 112', 112" coupled to or integrally formed with the body 114, 114', 114".

Figure 1A:
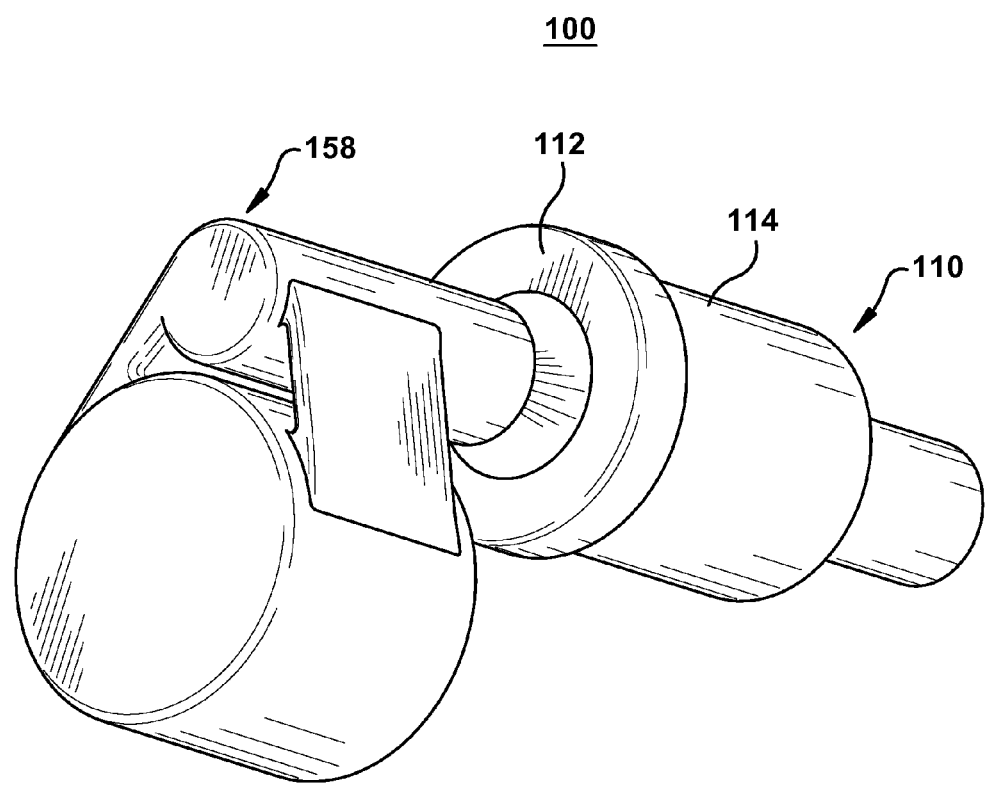
FIGS. 1A, 1B, 1C, 1D, 1E, 1F and 1G are views of pressure release systems according to embodiments of the present invention.
Figure 1B:
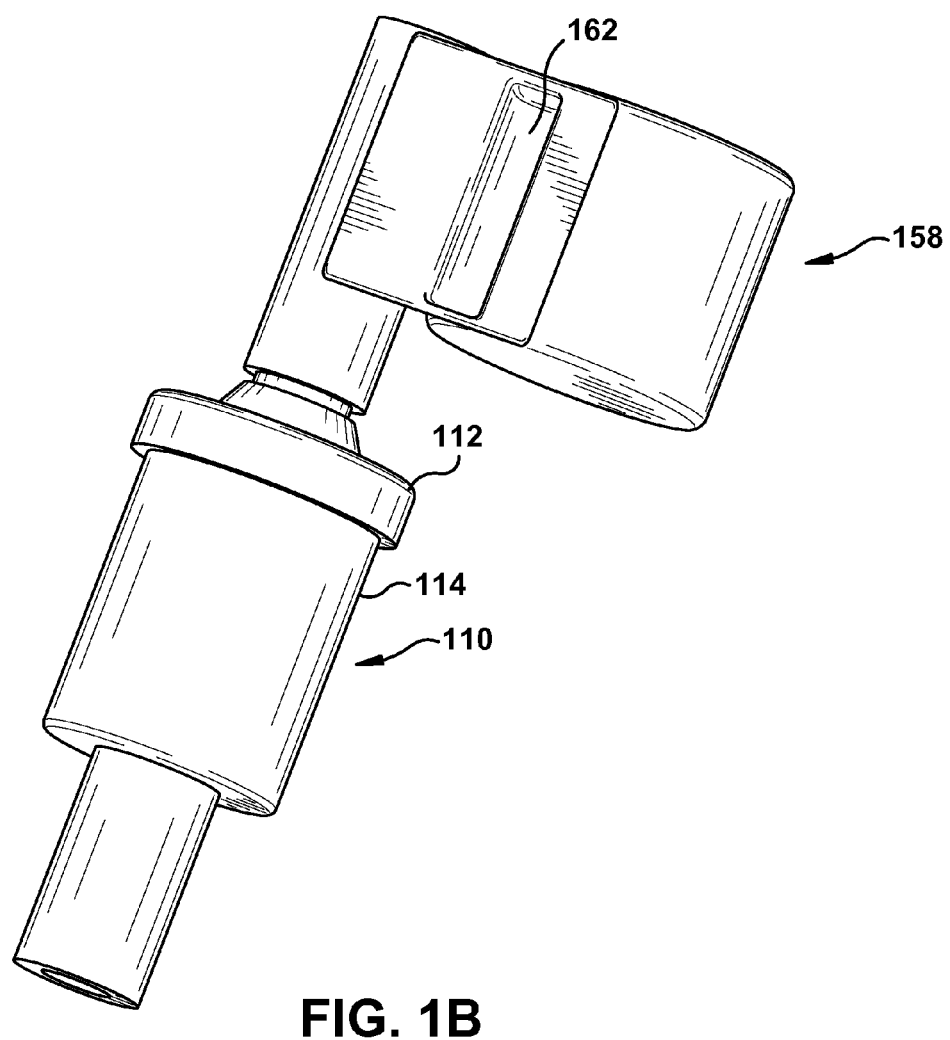
Figure 1C:
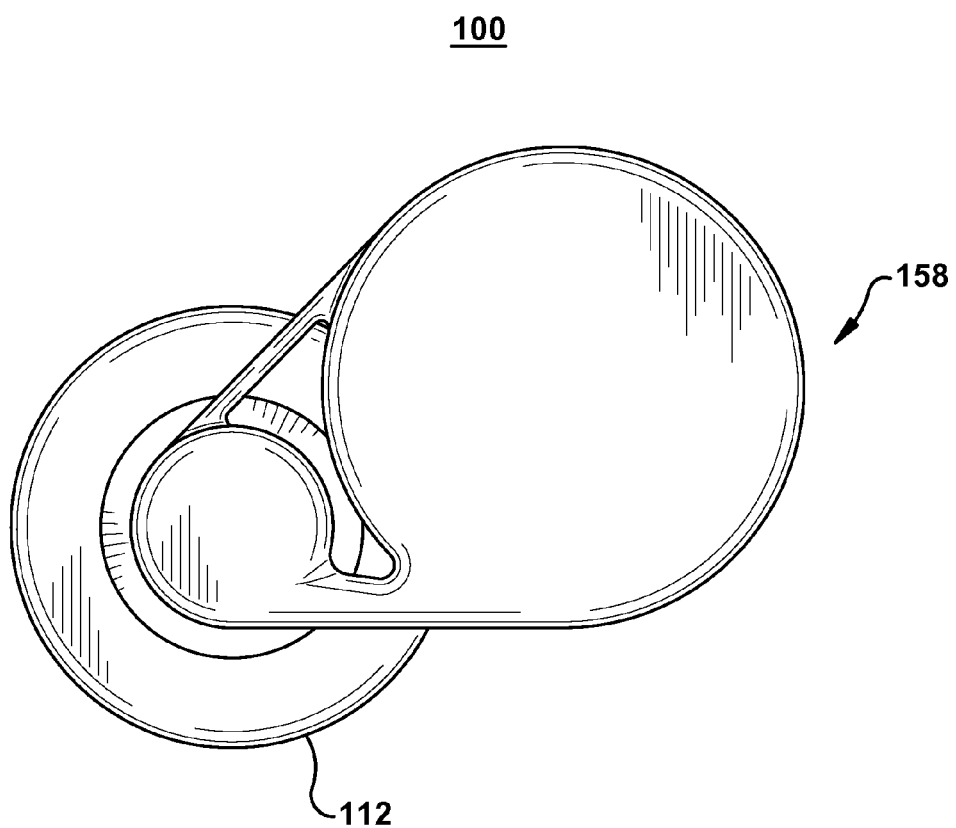
Figure 1D:
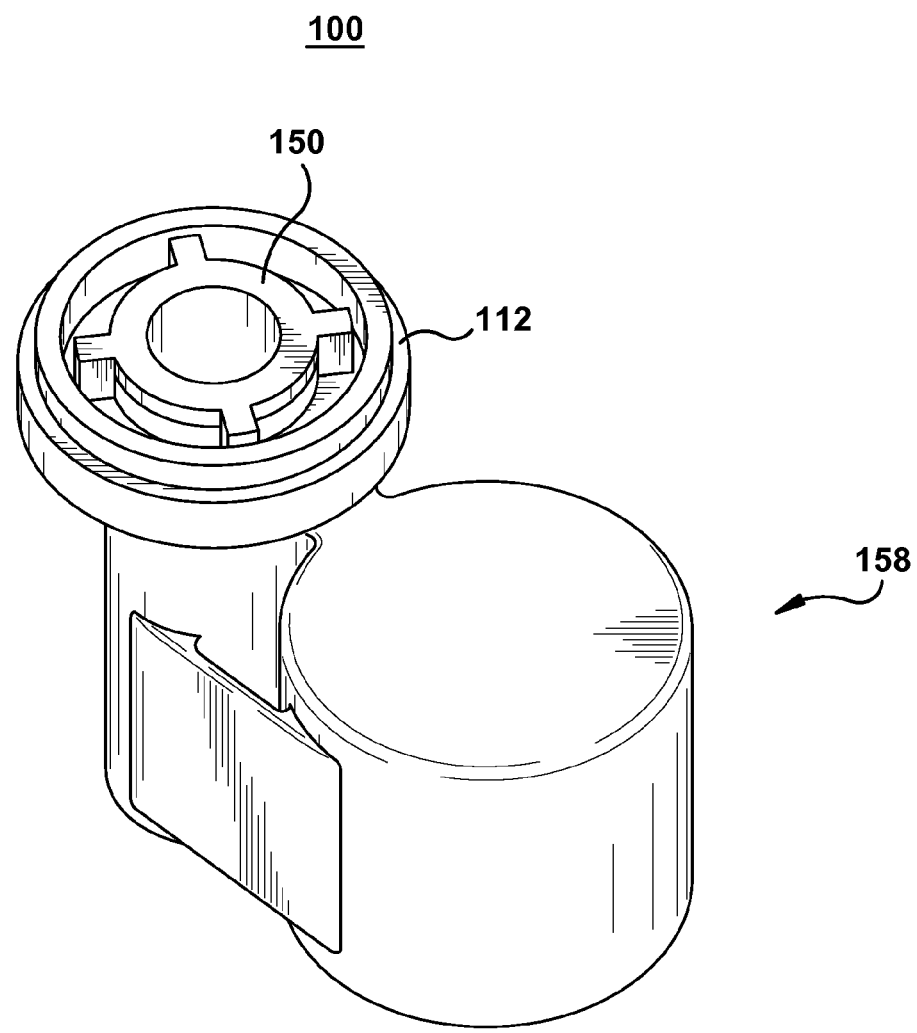
Figure 1E:
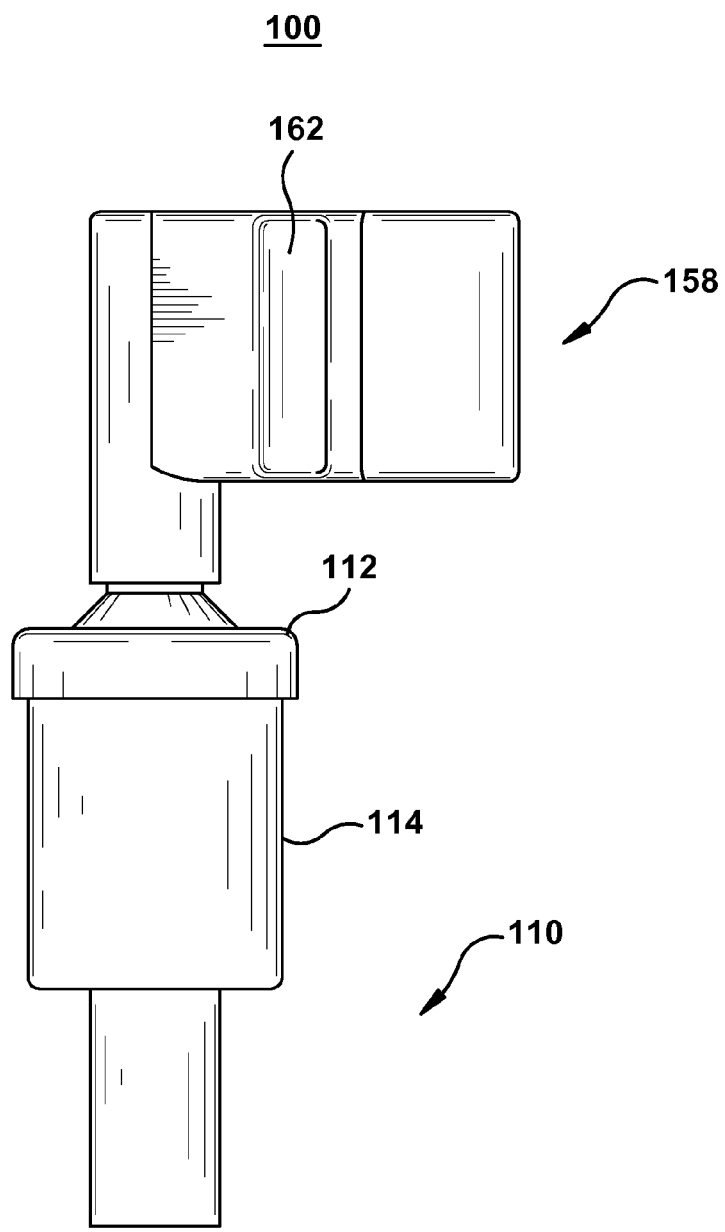
Figure 1F:
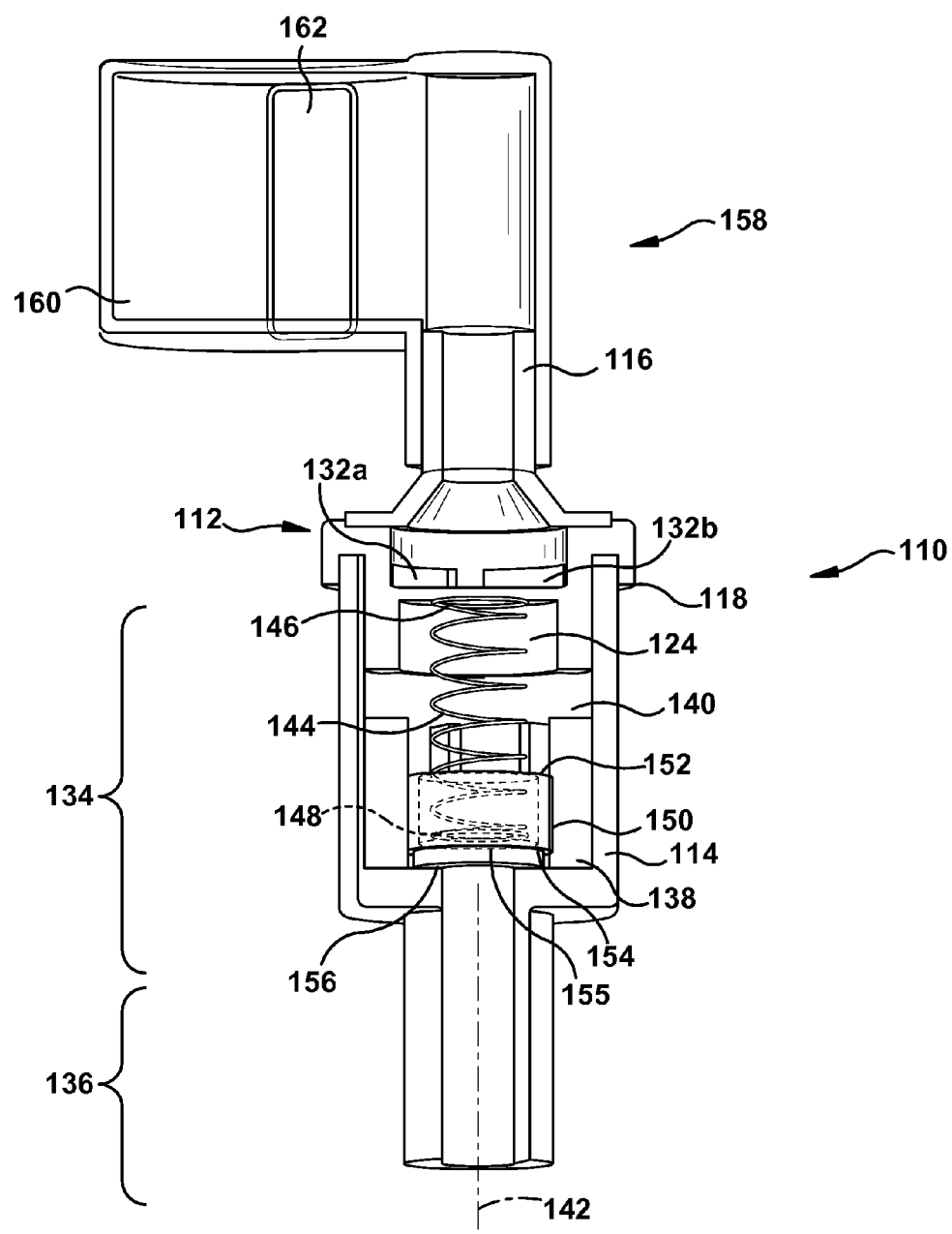
Figure 1G:
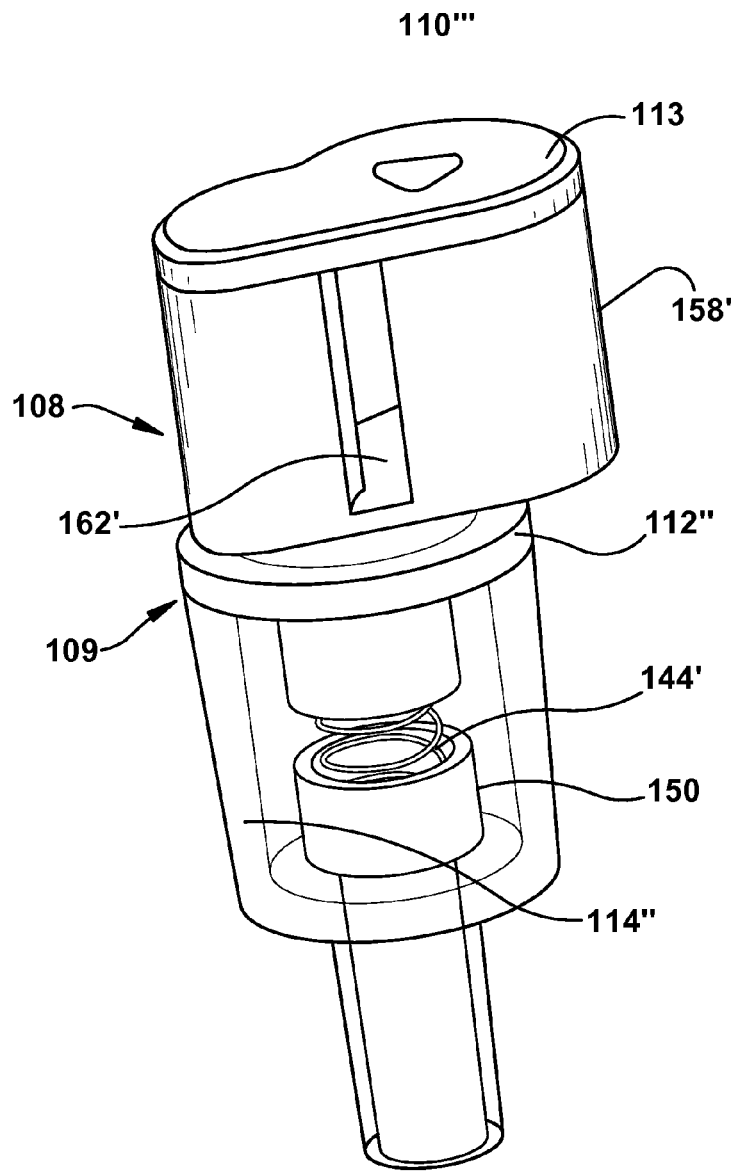
Figure 2A:
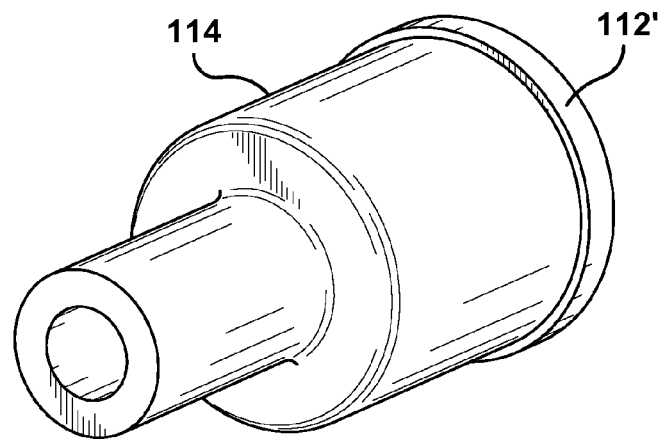
FIGS. 2A, 2B, 2C and 2D are views of pressure release systems according to embodiments of the present invention.
Figure 2B:
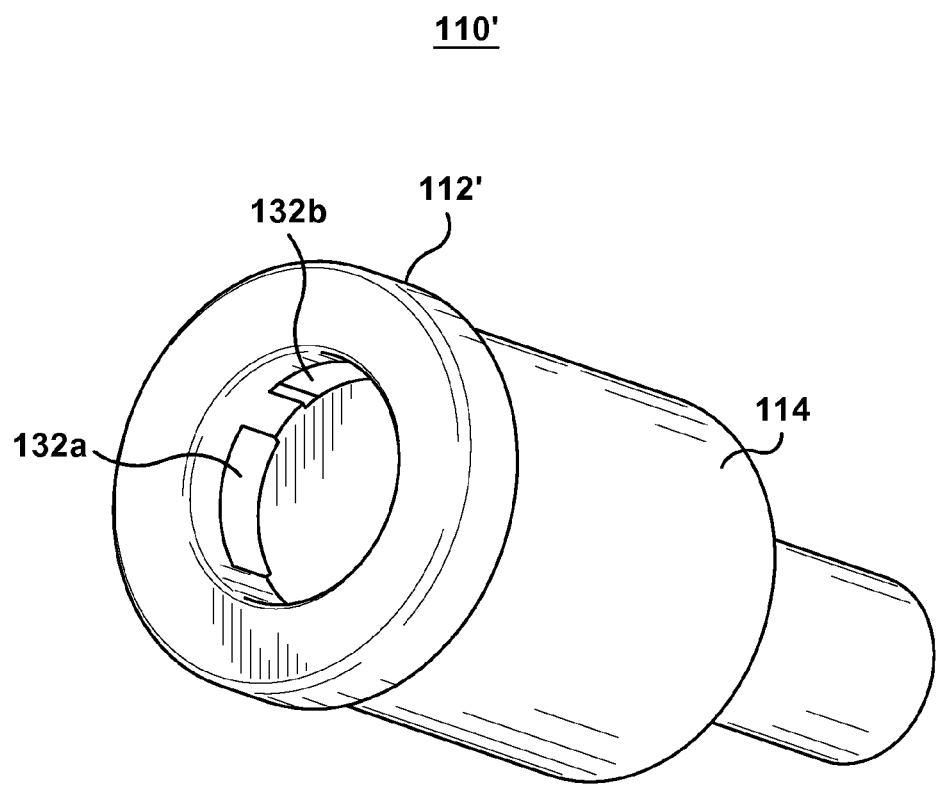
Figure 2C:
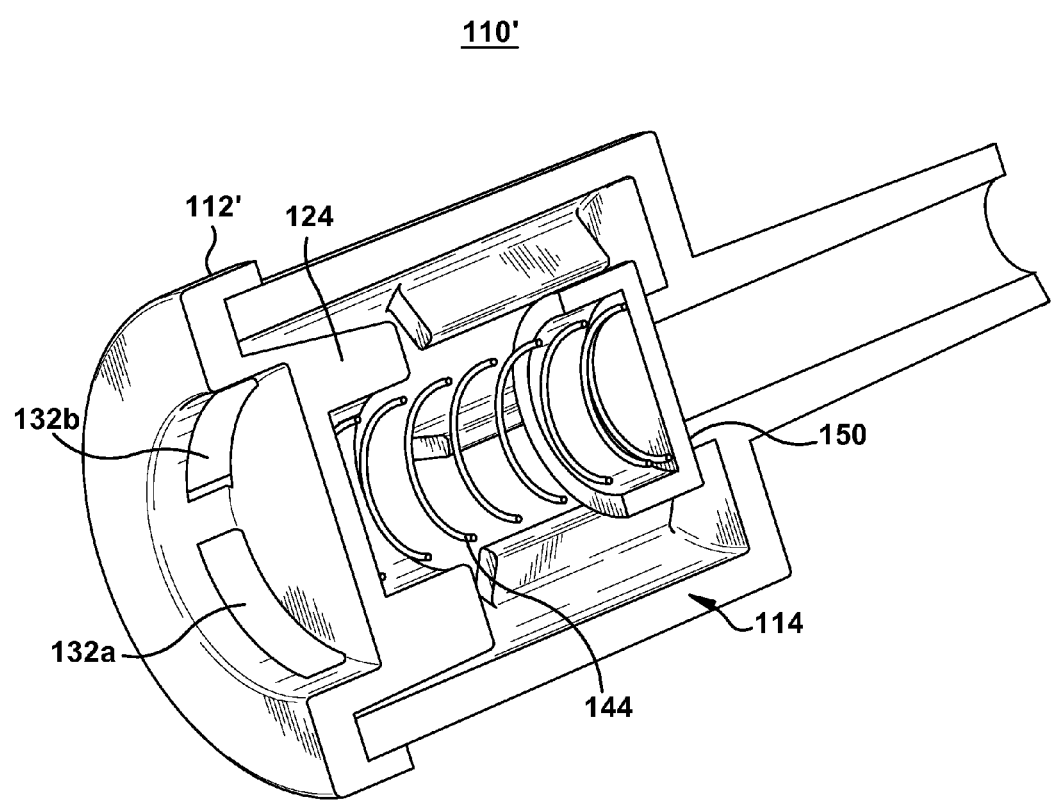
Figure 2D:
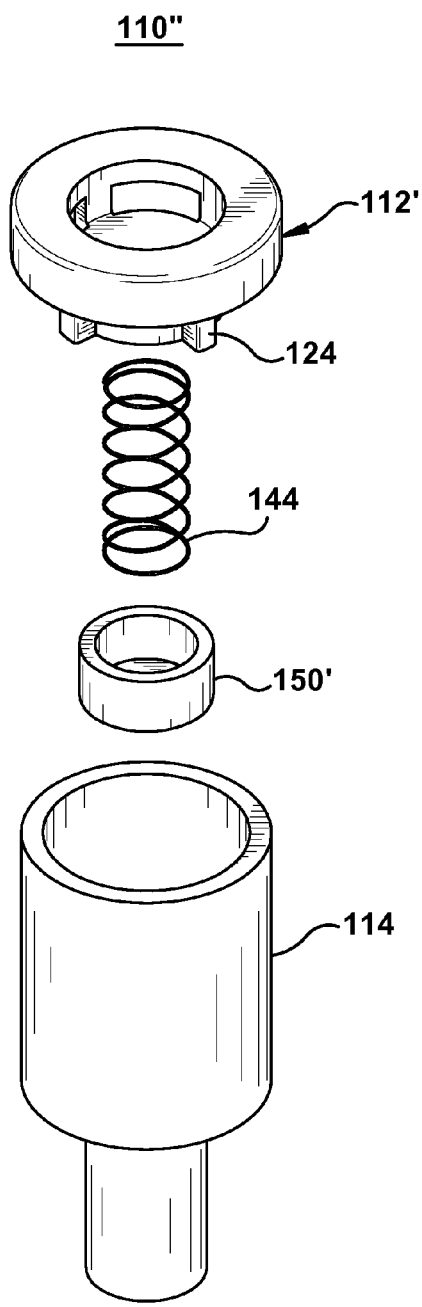

Referring to FIG. 1G, the pressure release valve 110' can include a cap 112", body 114", interior cap 150, compression spring 144', audible apparatus 158', and/or an audible apparatus cap 113. As shown, the audible apparatus 158' can be coupled to the body 114" by having a base of the audible apparatus 158' rest directly on the top portion 109 of the body 114" with no intervening neck portion of the audible apparatus raising it above the body 114" as seen in FIG. 1A, for example. As shown in FIG. 1A, a cylindrical portion of the audible apparatus 158 couples the audible apparatus 158 to the cap 112. By contrast, the pressure release valve 110' includes the audible apparatus 158' with no intervening corresponding cylindrical portion of the audible apparatus.

Rather, in the embodiment shown, the portion 108 of the audible apparatus immediately below the aperture 162' rests substantially flush on the top portion 109 of the body 114". In some embodiments, the audible apparatus 158' and the body 114" can be molded or welded together. As such, the profile of the pressure release valve 110' can be further reduced beyond those embodiments similar to that shown in FIG. 1A, for example, because the entire profile (e.g., area) of the pressure release valve 110''' is smaller in area, the audible apparatus 158' is not positioned as far away from the body 114" as in those embodiments, and/or the body 114" and the audible apparatus 158' are formed very closely together. In some embodiments, the body 114" and the audible apparatus 158' can be welded to one another. In other embodiments, the audible apparatus 158' can be coupled to the body 114" through other conventional methods including but not limited to, telescopic coupling of the two components, screw-on coupling of the two components, adhesive-based coupling of the two components or the like. In some embodiments, the pressure release valve 110''' can be a single, molded component. The design can reduce the likelihood that the pressure release valve 110''' will snag a patient or healthcare professional, the fabric or clothing provided on a patient or the healthcare professional and/or the respiratory circuit in which the pressure release valve 110''' is provided, and potentially reduce the likelihood of accidents.

Referring back to pressure release valves 110, 110', 110", 110''', in some embodiments, the body 114, 114', 114" can be ultrasonically welded to the cap 112, 112', 112". The body 114, 114', 114" can be ultrasonically welded to the cap 112, 112', 112" such that the weld is able to withstand a pull out force of 5.0 pounds.

The cap 112, 112', 112" and the body 114, 114', 114" can be formed of substantially rigid materials. In some embodiments, the cap 112, 112', 112" and/or the body 114, 114', 114" can be formed of polypropylene and/or polyethylene. In some embodiments, the cap 112, 112', 112" and/or the body 114, 114', 114" can be formed of only non-flammable materials and/or Bisphenol A.

Embodiments of the cap 112, 112' (and in some cases, 112") will now be described in greater detail. In some embodiments, the cap 112 can include a top portion 116 having a substantially solid surface and a bottom portion 118 dimensioned and shaped to couple snugly to the body 114, 114'. In some embodiments, the top portion 116 of the cap 112 can include a projection dimensioned and shaped to couple to the audible apparatus 158. By way of example, but not limitation, the projection can be substantially hollow and cylindrical. However, in other embodiments, the projection can be any shape coupleable to the audible apparatus 158.

In some embodiments, the cap 112, 112' can have one or more apertures 132a, 132b disposed therethrough and in fluid communication with an inner chamber 140 of the body 114, 114' when the cap 112' is coupled to or integrally formed with the body 114, 114'. The one or more apertures 132a, 132b can be in fluid communication with the interior region 164 of the audible apparatus 158 when the cap 112' is coupled to the audible apparatus 158.

While not shown in FIG. 1G, cap 112" can also include one or more apertures disposed therethrough and in fluid communication with an inner chamber 140 of the body 114" when the cap 112" is coupled to or integrally formed with the body 114". The one or more apertures (not shown) can be in fluid communication with the interior region of the audible apparatus 158' when the cap 112" is coupled to the audible apparatus 158'.

In various embodiments, the cap 112, 112', 112" can be operably and/or removably coupled to the audible apparatus 158 such that the cap 112, 112' is in fluid communication with an interior region 164 of the audible apparatus 158 (or, with reference to FIG. 1G, such that cap 112" is in fluid communication with an interior region (not shown) of the audible apparatus 158'). Referring back to pressure release valves 110, 110', 110", the bottom portion 118 of the cap 112, 112' can include a substantially stationary support structure 124. The cap 112, 112' can be adapted to be in fluid communication with the inner chamber 140 of the body 114, 114' when the cap 112, 112' is coupled to or integrally formed with the body 114, 114'.

The body 114, 114', 114' will now be described in greater detail. The body 114, 114' can be dimensioned and shaped to couple to the bottom portion 118 of the cap 112, 112'. As shown in FIG. 1G, the body 114" can be dimensioned and shaped to couple to the bottom portion 108 of the cap 112". Referring back to pressure release valves 110, 110', 110", 110''', in some embodiments, the top portion of the body 114, 114', 114" can be formed as a first tubular portion 134 having a first diameter while the bottom portion of the body 114, 114', 114" can be formed as a second tubular portion 136 having a second diameter. In some embodiments, the second diameter can be less than the first diameter.

Referring back to pressure release valves 110, 110', 110", 110''', in some embodiments, the body 114, 114', 114" can be any number of shapes or dimensions such that the pressure release valve 110, 110', 110" detects the pressure of gas received at the pressure release valve 110, 110', 110" and opens when the received gas has a pressure greater than or equal to the activation pressure (or, in some embodiments, open at a pressure that is greater than or equal to the activation pressure+a margin of error that is +/−5-15% of the activation pressure).

The inner chamber 140 of the body 114, 114' can be located in the first tubular portion 134 and can be in fluid communication with the interior region of the second tubular portion 136. Accordingly, a gas received in the second tubular portion 136 can flow into the inner chamber 140, thereby allowing the gas to flow to the patient instead of flowing into the atmosphere outside of the pressure release valve.

The inner chamber 140 of the body 114, 114', 114" can include a compression spring 144, 144'. As shown for pressure release valves 110, 110', 110" (but also applicable for pressure release valve 110"), the compression spring can have a first end 146, and a second end 148 distal from the first end 146. The compression spring can be designed to operate according to a number of different tensions and thereby be configurable to provide different activation pressures with minimum changes in the components composing the pressure release valve 110, 110', 110", 110'''. By offering the pressure release valve 110, 110', 110", 110''' at different activation pressures, the healthcare professional can select the best possible pressure release valve 110, 110', 110", 110''' (of a plurality of pressure release valves having different activation pressures) or the best possible activation pressure of a single pressure release valve 110, 110', 110", 110''' configurable to operate according to different activation pressures.

As shown for pressure release valves 110, 110', 110" (but the structure or functionality of which can apply to pressure release valve 110'''), the inner chamber 140 can also have an interior cap 150 with a first surface 152 and a second surface 154 opposite the first surface 152. In some embodiments, the inner chamber 140 can also include one or more interior cap support structures 138 adapted to cause the interior cap 150 to move along the axis 142 of the inner chamber when the force exerted on the interior cap 150 by the compression spring 144 changes. The interior cap 150 can move from a first position upward to a second position when the pressure of the gas is greater than or equal to the activation pressure of the pressure release valve 110, 110', 110" (or, in some embodiments, move from a first position upward to a second position at a pressure that is greater than or equal to the activation pressure+a margin of error that is +/−5-15% of the activation pressure).

The first end 146 of the compression spring 144 can be coupled to the support structure 124 of the cap 112, 112', and the second end 148 can be coupled to the first surface 152 of the interior cap 150.

The compression spring 144, 144' can be formed of stainless steel. The interior cap 150 can be formed of polypropylene, polyethylene, only non-flammable materials and/or Bisphenol A. The cap 112, 112', 112" and the interior cap 150 can be substantially transparent and smooth in some embodiments. In various embodiments, the cap 112, 112', 122", body 114, 114', 114", interior cap 150 and/or compression spring 144, 144' can have at least 0.005 inch diameter edge breaks.

The compression spring 144, 144' can be configured such that the compression spring 144, 144' exerts a downward force on the interior cap 150 such that the second surface 154 of the interior cap 150 is pressed against the port 156 of surface 155 reducing and/or preventing fluid communication of the gas received at the pressure release valve 110, 110', 110", 110''' into the inner chamber 140. Specifically, the compression spring 144, 144' can exert such downward force when the pressure of the gas received at the second tubular portion 134 is less than the activation pressure.

When a gas having a pressure greater than or equal to the activation pressure of the pressure release valve 110, 110', 110", 110''' is received (or, in some embodiments, when a gas having a pressure that is greater than or equal to the activation pressure+a margin of error that is +/−5-15% of the activation pressure is received), the force of the compression spring 144, 144' can be overcome by the force from the pressure of the gas, and the compression spring 144, 144' can be reduced in length thereby allowing the interior cap 150 to move toward the cap 112, 112', 112". Accordingly, as shown for pressure release valves 110, 110', 110" (but the structure or functionality of which can apply to pressure release valve 110'''), the port 156 in the surface 155 can be unblocked and the gas received in the second tubular portion 136 can flow into the inner chamber 140. The gas can then be emitted from the cap 112, 112', 112" to the interior region 164 of the audible apparatus 158, 158'. The audible apparatus 158, 158' can generate a sound when the gas is emitted from the audible apparatus 158, 158'. As such, the audible sound can alert healthcare professionals to overpressurization and, potentially, a need for corrective action with regard to the respiratory circuit coupled to the pressure release valve. After the pressure of the gas in the second tubular portion 136 is less than the activation pressure, the pressure release valve 110, 110', 110", 110''' can close. When the pressure release valve 110, 110', 110", 110''' is closed, gas received at the pressure release valve 110, 110', 110", 110''' can be provided to the patient because the gas can follow the path of least resistance and thereby travel past the pressure release valve 110, 110', 110", 110''' to the patient.

The weight of the combined pressure release valve 110, 110', 110", 110''' and/or audible apparatus 158, 158' can be such that the stress added to the respiratory circuit to which they can be coupled, can be minimized. Similarly, the pressure release valve 110, 110', 110", 110''' can be a low-profile such that the likelihood can be reduced that the pressure release valve 110, 110', 110", 110''' can physically interfere with, collide with, and/or displace a portion of a respiratory circuit to which the pressure release valve 110, 110', 110", 110''' can be coupled. By way of example, but not limitation, low-profile pressure release valve 110, 110', 110", 110''' can include those having configurations that have no projections jutting out from the body 114, 114', 114" and/or those that have a width and height that are less than or equal to 4 inches and 6 inches, respectively.

Embodiments of the audible apparatus 158 of the pressure release system 100, 100' shall now be described in detail. The audible apparatus 158 can have an exterior surface 160 and a substantially hollow interior region 164. An aperture 162 can be formed through the exterior surface 160 thereby providing fluid communication of received gas from the interior region 164 to the atmosphere outside of the audible apparatus 158.

The interior region 164 can be in fluid communication with the cap 112, 112'. The audible apparatus 158 can be coupled to the cap 112, 112' such that gas emitted from the cap 112, 112' can be received in the interior region 164 of the audible apparatus 158 and emitted from the audible apparatus 158 through the aperture 162.

The audible apparatus 158 can include an aperture and can be configured to receive gas and emit the gas through the aperture such that a sound emanates from the audible apparatus 158 notwithstanding the gas is of a relatively low pressure. In various embodiments, a relatively low pressure can be a pressure having a value between 0 and 20 cm $H_2O$.

In various embodiments, the audible apparatus 158 can be an apparatus that generates a sound that is between 40 and 50 decibels, between 40 and 60 decibels, between 40 and 80 decibels, or at least 40 decibels. In some embodiments, the audible apparatus 158 can be any apparatus capable of generating a sound that is typically audible to humans less than one year old to 70 years old. In some embodiments, the audible apparatus 158 can be any apparatus capable of generating a sound having a frequency between 15 and 22,000 Hertz. In some embodiments, the audible apparatus 158 can be adapted to generate a high-pitched shrill sound. In various embodiments, the audible apparatus can be a whistle or a horn.

Emitting gas from the audible apparatus 158 can therefore generate a sound that can alert a healthcare professional to the detection of excessive pressure by the pressure release valve 110, 110', 110", 110'''.

In some embodiments, the pressure release system (not shown) can also include a male luer fitting (not shown) coupled to or integrally formed with the pressure release system such that the pressure release system can be inserted into a standard-sized temperature probe adapter typically found in a CPAP or an HFNC respiratory circuit. In some embodiments, the male luer fitting can have an outer diameter (O.D) of approximately 7.5 mm. The small size of the male luer fitting can allow the pressure release system to fit into the 7.5 mm port of the adapter 530, 530' for use of the pressure release system inline in a respiratory circuit.

In some embodiments, the male luer fitting can have an internal diameter (I.D.) of approximately 4.7 mm. In various embodiments, the male luer fitting can be designed in compliance with ISO 594-2 and/or include a conical fitting with 6% luer taper.

The male luer fitting can allow the pressure release valve to accept a straight tee adapter and be inserted into a t-shaped pressure monitoring adapter supplied with a number of CPAP and HFNC circuits.

In some embodiments, the male luer fitting can fit securely into an adapter designed according to embodiments of the invention, and described below with reference to FIGS. 5A, 5B, 5C, 5D, 6A, and/or 6B. The fitting can fit securely such that there is substantially no gas leakage to the atmosphere at the point at which the fitting is coupled to the adapter 530, 530'.

In other embodiments (not shown), a pressure release valve (not shown) can include a body having an inner chamber, a compression spring, an interior cap, a port and first and second tubular portions such as that described with reference to FIG. 1F. In some embodiments, the pressure release valve can include a magnet in lieu of a compression spring, as described above. In either of the foregoing embodiments, the pressure release valve can have an audible apparatus integrally formed with or on the body. The audible apparatus can have an aperture formed therethrough such that gas received in the body can be emitted through the aperture to the atmosphere. The audible apparatus can generate a sound upon emitting the gas through the aperture.

In various embodiments, the audible apparatus can be formed within or on the body such that the aperture is provided on a side or a top surface of the body, and a port in fluid communication with the interior region of the body can be in fluid communication with the aperture. For example, the audible apparatus can be formed as a cover having an aperture positioned over an opening of the body such that gas emitted from the body can be emitted through the aperture.

In some embodiments, the audible apparatus can be formed on the body in fluid communications with an opening on the body. The opening on the body can be at the top portion of the body or on the first or second tubular portions of the body.

In various embodiments, the body can have a substantially equal diameter from the top portion of the body to the body portion of the body. In these embodiments, the audible apparatus does not protrude from the body.

In some embodiments, the top portion (or other portion) of the body can be a selected color indicative of the pressure of the pressure release system. By way of example, but not limitation, the color can be red, yellow or green to indicate a pressure release system adapted to indicate activation pressures of 60 cm $H_2O$, 40 cm $H_2O$ and 20 cm $H_2O$, respectively.

With reference to the respiratory circuit 700 in FIG. 7 and FIGS. 1A, 1B, 1C, 1D, 1E, 1F, 1G and/or 1H, and other respiratory circuits, the pressure release system 100, 100', 100'' (or pressure release system 710, 710') can be positioned proximal to the patient in some embodiments as shown. Such positioning of the pressure release system 100, 100', 100'' (or pressure release system 710, 710') can provide significant improvements in accuracy in the pressure experienced by a patient. While the pressure release system 100, 100', 100'' (or pressure release system 710, 710') can alternately (or additionally) be provided proximal to a humidifier 730 of the respiratory circuit, such positioning disadvantageously and primarily protects the circuits instead of the patient, by measuring the pressure experienced in the circuit tubing shortly after gas leaves the gas source 720.

In one or more of these embodiments, the functionality and/or structure of the audible apparatus can replace the functionality and/or structure of the cap 112, 112'.

Yet another embodiment of the pressure release valve (not shown) can be provided. In one or more embodiments, the functionality of the above-referenced pressure release valves 110, 110', 110'', 110''' and the functionality of the above-referenced audible apparatus 158 can be provided in pressure release portion and the audible portion of the pressure release valve (not shown). The pressure release valve can include a pressure release portion of the pressure release valve and an audible portion of the pressure release valve.

In some embodiments, the pressure release valve can include one or more of the components or functionalities of the pressure release valve 100, 100', 100'' (or any other pressure release valve described herein) and/or the audible apparatus 158. For example, the pressure release valve can be configured with activation pressures and with the ability to emanate a sound when a gas is received that is greater than or equal to the activation pressure (or greater than or equal to the activation pressure+/−a margin of error of 5-15% of the activation pressure).

In some embodiments, the audible portion can be formed in an interior region of the pressure release portion such that all or part of the audible portion is recessed or enclosed within the pressure release portion. As such, in embodiments wherein the entire audible portion is enclosed within the pressure release portion, the audible portion is not viewable from a side view of the pressure release valve. In some of these embodiments, the audible portion is also not viewable from a top view of the pressure release valve. In some embodiments, while the audible portion is not viewable from a side view of the pressure release valve, the audible portion may be recessed within the pressure release portion but viewable from a top view of the pressure release valve.

In some embodiments, the pressure release portion can include a body having an inner chamber, a compression spring, an interior cap, a port and first and second tubular portions such as that described with reference to FIG. 1F. In various embodiments, the body can have a substantially equal diameter from the top portion of the body to the body portion of the body. In these embodiments, the audible apparatus can also re complete recessed or enclosed within the body of the pressure release portion. In some embodiments, the pressure release portion can include a magnet in lieu of a compression spring, as described above.

In either of the foregoing embodiments, the audible portion can be formed as a single component with the pressure release portion and have an aperture formed therethrough such that gas received in the body can be emitted through the aperture to the atmosphere. The audible portion can emanate a sound upon emitting the gas through the aperture.

In some embodiments, the top portion (or other portion) of the body can be a selected color indicative of the pressure of the pressure release valve. By way of example, but not limitation, the color can be red, yellow or green to indicate a pressure release valve adapted to indicate activation pressures of 60 cm $H_2O$, 40 cm $H_2O$ and 20 cm $H_2O$, respectively.

The aforementioned embodiments can reduce the profile of the pressure release valve and reduce the likelihood that the pressure release valve will snag the patient, clothing or fabric near the patient, the incubator, or isolette, or medical chamber or any tubing or components of the respiratory breathing circuit in which the pressure release valve can be provided. In some embodiments, the pressure release valve can be approximately 1 inch in height. In other embodiments, the pressure release valve can be less than 1 inch in height. In some embodiments, the pressure release valve can be lightweight so as to reduce the amount of stress on the respiratory circuit relative to models of valves that may not be lightweight. In some embodiments, the lightweight pressure release valve can be approximately 10 grams. In some embodiments, conventional pressure release valves can be 40-50 grams. As such, a lightweight device can be one that is 10 grams and/or approximately 20-25% of the weight of the conventional valves or systems, which can be 40-50 grams.

FIGS. 5A, 5B, 5C and 5D are views of pressure release systems according to embodiments of the present invention.

Figure 6A:
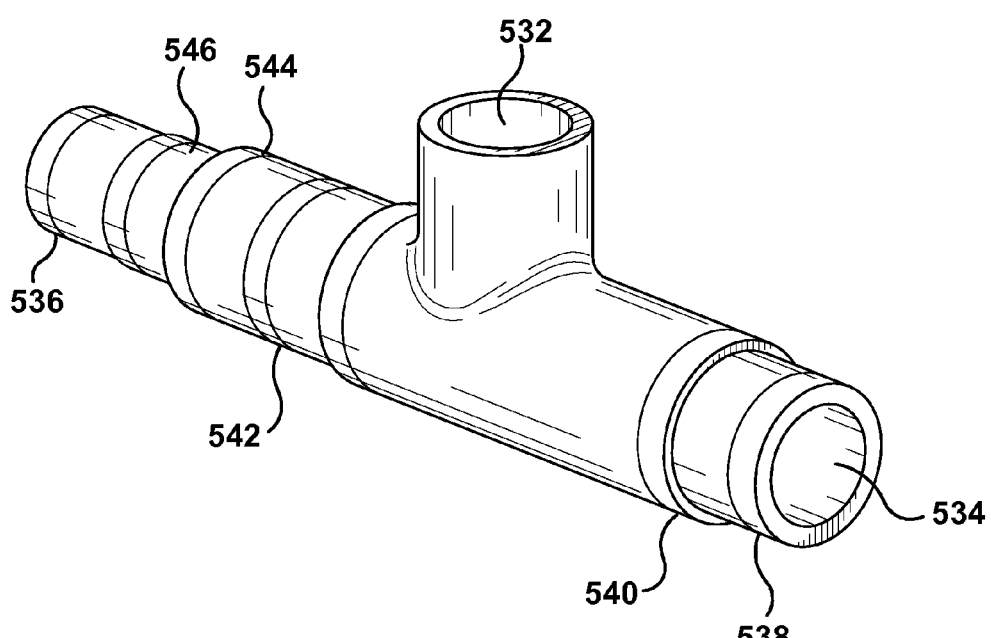
FIGS. 6A and 6B are views of adapters according to embodiments of the present invention.
Figure 6B:
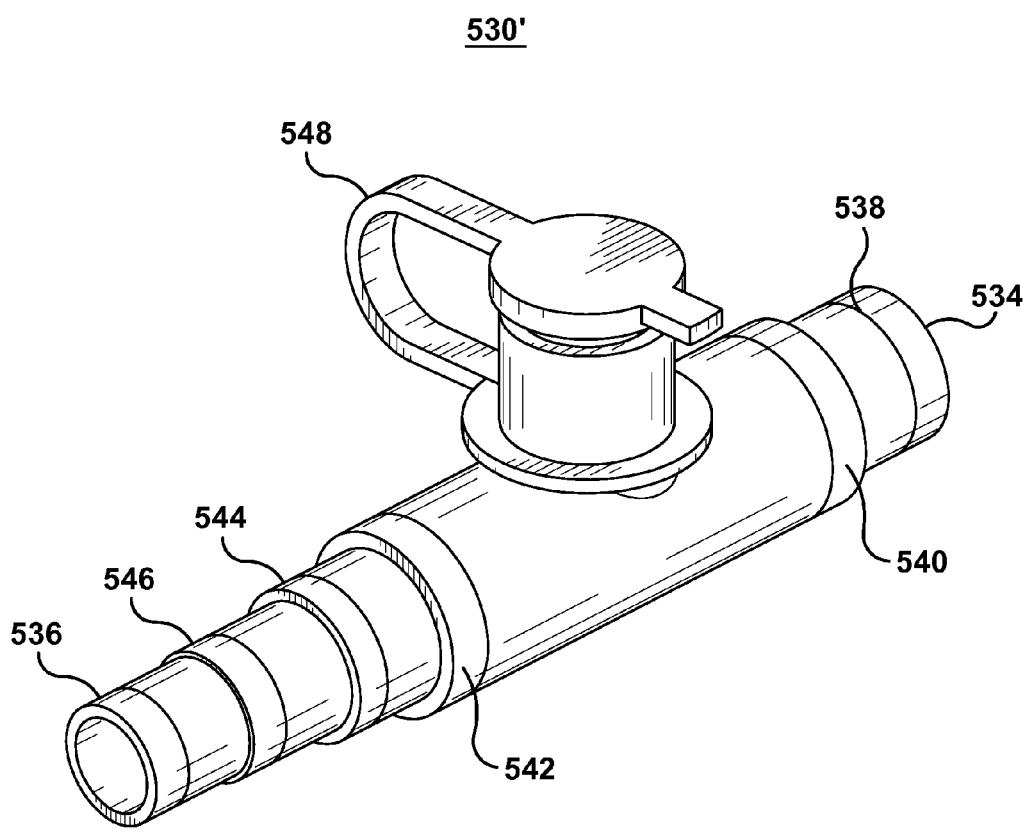

FIGS. 6A and 6B are views of adapters according to embodiments of the present invention.

The pressure release system 500 can include a pressure release valve 510, an audible apparatus 520 and an adapter 530, 530'. In various embodiments, the pressure release valve 510 can be any embodiment of the pressure release valves 110, 110', 110'', 110''' described with reference to FIGS. 1A, 1B, 1C, 1D, 1E, 1F, 1G, 2A, 2B, 2C, 2D, 3A and/or 3B. The audible apparatus 520 can be any embodiment of the audible apparatus 158, 158' (or the above-described audible portion) described with reference to FIGS. 1A, 1B, 1C, 1D, 1E, 1F, 1G, 4A, 4B and/or 4C. The arrangement, integration, coupling and/or functionality of the pressure release valve 510 and the audible apparatus 520 with one another can be as any embodiment of the pressure release system 100, 100' described with reference to FIGS. 1A, 1B, 1C, 1D, 1E, 1F, 1G and/or can include aspects of the embodiments described with reference to FIGS. 2A, 2B, 2C, 2D, 3A, 3B, 4A, 4B, and/or 4C.

The adapter 530, 530' of pressure release system 500 can be coupled to or integrally formed with the pressure release valve 510 (or any of the aforementioned pressure release systems). The pressure release valve 510 (or any of the aforementioned pressure release systems) can be in fluid communication with audible apparatus 520 such that the gas received in the pressure release valve 510 (or any of the aforementioned pressure release systems) can be emitted to the audible apparatus 520 and the audible apparatus 520 can emit a volume of the gas, and generate a sound to alert the healthcare professional of excessive pressure.

The adapter 530, 530' will now be described in greater detail. The adapter 530, 530' can be formed of a substantially rigid material and can have an interior region that is substantially hollow. The interior region can be in fluid communication with the pressure release valve 510 (or any of the aforementioned pressure release systems) when the adapter 530, 530' is coupled to or integrally formed with the pressure release valve 510 (or any of the aforementioned pressure release systems).

In some embodiments, the adapter 530, 530' can include indicia of the proper orientation of the adapter 530, 530' between two or more physical elements such that gas flows through the adapter 530, 530' in the proper direction from right to left or left to right, depending on the orientation of the adapter 530, 530'. By way of example, but not limitation, the indicia can include arrows and/or lettering.

In some embodiments, the adapter 530, 530' can have one or more connectors and be any adapter adapted to be coupleable to one or more physical elements having one or more I.D. and/or O.D. complementary to one or more of the connectors. In one embodiment, the adapter 530, 530' is an adapter adapted to be coupleable to six or more different I.D.s and/or O.D.s. In some embodiments, the adapter 530, 530' can include connectors that can be shaped as conical fittings. In some embodiments, the conical fittings can have approximately 6% taper (ISO 594-2).

While the adapter 530, 530' shown can be T-shaped, adapters and/or connectors can be any number of shapes suitable for coupling a physical element to the adapter 530, 530'.

In various embodiments, the adapter 530, 530' can have a first connector 5320 that is coupleable to the pressure release valve 510 (or any of the aforementioned pressure release systems) and a second connector 534 that is coupleable to an inspiratory limb or extension of a respiratory circuit. By way of example, but not limitation, the extension of the respiratory circuit can be a nasal cannula, nasal prongs and/or any other type of tubing and/or adapters typically used in respiratory circuits. In various embodiments, the first connector 532 and/or the second connector 534 can be coupleable to the pressure release valve 510 (or any of the other aforementioned pressure release systems) and/or the inspiratory limb or extension of the respiratory circuit by an intervening extension tube or any number of components typically used in a respiratory circuit.

The adapter 530, 530' can be provided with the pressure release valve or separate from the pressure release valve. The adapter can couple securely to the inspiratory and the expiratory tubing of the pressure release system such that there is substantially no gas leakage into the atmosphere at the point at which the adapter 530, 530' is coupled to the inspiratory or expiratory tubing.

In another embodiment, the adapter 530, 530' can have a first connector 532 that is coupleable to the pressure release valve 510 (or any of the aforementioned pressure release systems), a second connector 534 that is coupleable to an inspiratory limb or extension of a respiratory circuit and/or a third connector 536 that is coupleable to an expiratory limb or extension of a respiratory circuit. In various embodiments, the extension of a respiratory circuit can include, but is not limited to, a nasal cannula, nasal prongs and/or other components or tubing typically used in a respiratory circuit.

The adapter 530, 530' can include a first connector 532 that can be of a dimension and shape to be coupleable to the pressure release valve 510 (or any of the aforementioned pressure release systems) as a female coupling or as a male coupling. In some embodiments, the adapter 530, 530' can also include a second connector 534 and a third connector 536 that can be of a dimension and shape to be coupleable to physical elements that can be included in a respiratory circuit. Further, in some embodiments, as shown, the adapter 530, 530' can also include an O.D. second connector 538, a fourth connector 540, a fifth connector 542, a sixth connector 544 and/or a seventh connector 546 designed with a pre-configured O.D. for coupling to a respiratory circuit extension. In one embodiment, as shown in FIG. 6B, the adapter 530, 530'' can have a cap 548 adapted to cover the first connector 532.

In various embodiments, the I.D. and/or O.D. can differ for one or more of the connectors 532, 534, 536, 538, 540, 542, 544, 546. Accordingly, one or more of the connectors can be formed with dimensions suitable for I.D. connection (e.g., coupling the adapter 530, 530' as a female) or for O.D. connection (e.g., coupling the adapter 530, 530' as a male) to a physical element. The adapter 530, 530' can therefore be suitable for use with any number of respiratory circuits having components manufactured by different companies, including, but not limited to, FISHER & PAYKEL® components and/or HUDSON RESPIRATORY RCI® components. The respiratory components can include, but are not limited to, nasal cannula, nasal prongs, tubing and/or another adapter.

Exemplary embodiments of the connectors 532, 534, 536, 538, 540, 542, 544, 546 can be designed and sized as detailed in Table 1.

TABLE 1

| Connector Reference Numeral | Coupling of Physical Element | Description of Coupling | Diameter of Connector (mm) | Exemplary Physical Element for Connector Coupling |
|---|---|---|---|---|
| 532 | I.D. | I.D. connection (adapter as female) to pressure release valve (primary connection) | 7.5 | WET NOSE TECHNOLOGIES ™ pressure release valve or temperature probe |
| 534 | I.D. | I.D. connection (adapter as female) from circuit side | 7.5 | Generic inspiratory limb or extension for connectors |
| 536 | | O.D. connection (adapter as male) from patient side | 7.5 | FISHER & PAYKEL ® infant or neonate nasal cannula(s) VAPORTHERM ® infant or neonate nasal cannula(s) Neonate nasal cannula sold by Salter Labs |
| 538 | O.D. | O.D. connection (adapter as male) from circuit side | 10 | FISHER & PAYKEL ® inspiratory limb or extension for connectors |
| 540 | O.D. | O.D. connection (adapter as male) from circuit side | 11.7 | HUDSON RCI ® inspiratory limb for connector |
| 542 | O.D. | O.D. connection (adapter as male) | 10.3 | FISHER & PAYKEL ® or generic tubing for its connectors |
| 544 | O.D. | O.D. connection (adapter as male) from patient side | 10 | FISHER & PAYKEL ® or BNCPAP expiratory limb or extension for connectors |
| 546 | O.D. | O.D. connection (adapter as male) from patient side | 8.5 | HUDSON RCI ® infant or premature/neonate nasal cannula(s) |

Various embodiments of the connectors 532, 534, 536, 538, 540, 542, 544, 546 will now be further described. The first connector 532 can have an I.D. of approximately 7.5 mm for I.D. connection to a physical element of a respiratory circuit. In some embodiments, the physical element can be the WET NOSE TECHNOLOGIES™ pressure release valve 510 or a HUDSON RCI® temperature probe.

The second connector 534 can have an I.D. of approximately 7.5 mm for I.D. connection to a physical element of a respiratory circuit. By way of example, but not limitation, the physical element can be an inspiratory limb or extension of the respiratory circuit and/or a standard wye fitting. In various embodiments, the second connector 534 can have any I.D. adapted to couple to an inspiratory limb or extension of the respiratory circuit and/or a standard wye fitting. In various embodiments, an extension of the respiratory circuit can include a nasal cannula, nasal prongs and/or any other components typically used in a respiratory circuit.

The O.D. second connector 538 can have an O.D. of approximately 10 mm and/or can be configured to be any outer diameter for providing an O.D. connection to a physical element of a respiratory circuit. The physical element can be the FISHER & PAYKEL® inspiratory limb or extension. In some embodiments, the O.D. second connector 538 can have any O.D. adapted to couple to the FISHER & PAYKEL® inspiratory limb or extension. In some embodiments, an extension of the respiratory circuit can include a nasal cannula, nasal prongs and/or any other components typically used in a respiratory circuit.

The third connector 536 can be dimensioned for O.D. connection to a physical element connected to the patient. In some embodiments, the third connector 536 can be 7.5 mm and/or can be configured to be any outer diameter for providing an O.D. to a physical element such as a nasal cannula. By way of example, but not limitation, the physical element can be FISHER & PAYKEL® and/or VAPORTHERM™ nasal cannulas and/or nasal cannulas sold by Salter Labs. The nasal cannula can have an approximately 9 mm I.D. female fitting to the 7.5 mm male fitting of the third connector 536 in some cases due to the pliability of the conduit attached to the nasal cannula. In some embodiments, the third connector 536 can have any O.D. adapted to couple to the FISHER & PAYKEL® infant or neonate nasal cannulas, VAPORTHERM™ infant or neonate nasal cannulas and/or neonate nasal cannulas sold by Salter Labs.

The fourth connector 540 can have an O.D. of approximately 11.7 mm and/or can be configured to be any outer diameter for providing an O.D. connection to a physical element of a respiratory circuit. The physical element can be a HUDSON RCE® inspiratory limb. In some embodiments, the fourth connector 540 can have any O.D. adapted to couple to the HUDSON RCI® inspiratory limb.

The fifth connector 542 can have an O.D. of approximately 10.3 mm and/or can be configured to be any outer diameter for providing an O.D. connection to a physical element of a respiratory circuit or to a physical element connected to the patient. The physical element can be FISHER & PAYKEL®, HUDSON RCI®, generic tubing and/or a nasal cannula. In some embodiments, the fifth connector 542 can have any O.D. adapted to couple to a FISHER & PAYKEL®, HUDSON RCI® and/or generic tubing or a nasal cannula.

The sixth connector 544 can have an O.D. of approximately 10 mm and/or can be configured to be any outer diameter for providing an O.D. connection to a physical element connected to the patient. The physical element can be a FISHER & PAYKEL® and/or any continuous positive airway pressure respiratory circuit, high flow respiratory circuit, bi-level respiratory circuit, end/expiratory positive airway pressure respiratory circuit and/or inspiratory positive airway pressure respiratory circuit expiratory limb or extension. In some embodiments, the sixth connector 544 can have any O.D. adapted to couple to FISHER & PAYKEL® and/or any continuous positive airway pressure respiratory circuit, high flow respiratory circuit, bi-level respiratory circuit, end/expiratory positive airway pressure respiratory circuit and/or inspiratory positive airway pressure respiratory circuit expiratory limb or extension. In some embodiments, an extension of the respiratory circuit can include a nasal cannula, nasal prongs and/or any other components typically used in a respiratory circuit.

The seventh connector 546 can have an O.D. of approximately 8.5 mm and/or can be configured to be any outer diameter for providing an O.D. connection to a physical element connected to the patient. In some embodiments, the physical element can be a HUDSON RCI® infant, premature and/or neonate baby nasal cannula.

As discussed above, with reference to third connector 536, notwithstanding the above-referenced approximate I.D. and O.D. values for the adapter 530, 530', the physical elements to which the adapter 530, 530' can couple, can be pliable. Accordingly, a diameter of a portion of the physical element to which the one or more connectors 532, 534, 536, 538, 540, 542, 544, 546 of the adapter 530, 530' is coupled can be greater than or less than the diameter of the respective one or more connectors 532, 534, 536, 538, 540, 542, 544, 546, yet the one or more connectors 532, 534, 536, 538, 540, 542, 544, 546 can still be coupled to the physical element. For example, the fourth connector 538 can be coupled to a FISHER & PAYKEL® pliable inspiratory limb or extension through an O.D. connection. Accordingly, the fourth connector 538 can act as the male component in the coupling; however, the inspiratory limb or extension can be less than the O.D. of the fourth connector 538 and fit snugly with the fourth connector 538 due to the pliability of the inspiratory limb or extension. In some embodiments, an extension of the respiratory circuit can include a nasal cannula, nasal prongs and/or any other components typically used in a respiratory circuit.

In some embodiments of the invention, gas can be received in the second connector 534 of the adapter 530, 530'. The gas can be emitted to the pressure release valve 510 through the first connector 532 to which the pressure release valve 510 can be coupled. The pressure of the gas can be detected by the pressure release valve 510. If the pressure of the gas is greater than or equal to the activation pressure of the pressure release valve 510 (or, in some embodiments, if the pressure of the gas is greater than or equal to the activation pressure+a margin of error that is +/−5-15% of the activation pressure), the pressure release valve 510 can open and emit a volume of the received gas to the audible apparatus 520. The audible apparatus 520 can emit a volume of the received gas to the atmosphere outside of the pressure release system 500, and can generate a sound upon emitting the received gas. The pressure release valve 510 can continue to detect the gas in the pressure release valve 510, and can close after the pressure of the gas in the pressure release valve 510 is less than the activation pressure of the pressure release valve 510. While the pressure release valve 510 is closed, the gas received in the adapter 530, 530' can follow the path of least resistance by flowing out of the third connector 536 of the adapter 530, 530' toward the patient.

In some embodiments, the second connector 534 and the third connector 536 can be coupled within an inspiratory limb or extension of a respiratory circuit. In some embodiments, the adapter 530, 530' can be positioned within the limb or extension at a distance that is not more than 12 inches from the patient. In some embodiments, an extension of the respiratory circuit can include a nasal cannula, nasal prongs and/or any other components typically used in a respiratory circuit.

In some embodiments, the second connector 534 and the third connector 536 can be coupled within an expiratory limb, extension of a respiratory circuit and/or coupled to a temperature probe adapter, port, a pressure gauge adapter and/or any other type of adapter or component of the respiratory circuit allowing the pressure release valve 510 to detect the pressure of the gas that is being provided to the patient. In some embodiments, an extension of the respiratory circuit can include a nasal cannula, nasal prongs and/or any other components typically used in a respiratory circuit. In some embodiments, the adapter 530, 530' can be positioned within the limb or extension at a distance that is not more than 12 inches from the patient. In some embodiments, the adapter 530, 530' can include mounting configurations for mounting one or more of the following: thermometer/temperature sensor, fluid flow sensor, humidity sensor and/or pressure sensor.

In some embodiments, the adapter 530, 530' can be a single patient use medical device. The adapter 530, 530' can be disposable. In some embodiments, the adapter 530, 530' can also be supplied sterile.

In some embodiments, the adapter can be comprised of all non-flammable materials. In some embodiments, the adapter 530, 530' be solely mechanical and require no electrical components for operation. In some embodiments, the edges of each of the components of the adapter can have at least 0.005 inch diameter edge breaks to reduce the instances of sharp edges that may injure a patient or healthcare professional. The adapter can be configured to be able to couple to the pressure release system without supports that are external to the adapter.

A method of operation in accordance with the embodiments described herein is as follows. A gas is received at a pressure release valve, or at a pressure release system having a pressure release valve. When the gas pressure is less than the activation pressure+\−5% (or is less than the activation pressure), the compression spring applies a downward force on the interior cap causing the interior cap to remain in a seated position and preventing the gas from entering the inner chamber 140 of the pressure release valve 110, 110', 110", 110'''.

When the gas pressure is greater than or equal to the activation pressure (or, in some embodiments, if the gas pressure is greater than or equal to the activation pressure+/−a margin of error of 5-15% of the activation pressure), the interior cap 150 rises along axis 142 from a seated position thereby allowing the gas to enter the inner chamber 140. The pressure release valve 110, 110', 110", 110''' can emit the received gas to the atmosphere via the audible apparatus 158. When the gas is output from the audible apparatus 158, a sound can emanate from the audible apparatus 158 for alerting a healthcare provider that the gas line is providing a pressure that is above the activation pressure. When the gas pressure falls below the activation pressure, the pressure release valve 110, 110', 110", 110''' can close thereby reducing the gas emitted to the audible apparatus 158 and corresponding causing the audible sound to emanate.

When a gas pressure that is greater than a maximum gas pressure is detected at the pressure release valve 110, 110', 110", 110''' (or, in some embodiments, if a pressure that is greater than the maximum gas pressure+a margin of error that is +/−5-15% of the maximum gas pressure), the pressure release valve 110, 110', 110", 110''' can reduce the pressure to the activation pressure or to less than the activation pressure. In some embodiments, the maximum gas pressure is 60 cm $H_2O$ An embodiment of a pressure release system kit (not shown) shall now be described. Any of the aforementioned embodiments of pressure release systems, including pressure release valves, audible apparatus and/or adapters can be used in any arrangement of one or more components in the pressure release system kit. In embodiments, each pressure release valve and/or cap for the pressure release valve can include color coding to indicate the activation pressure for the pressure release valve. In various embodiments, the cap and/or body for pressure release valve that are adapted to have an activation pressure of 20 cm $H_2O$ can be green; the cap and/or body for pressure release valves that are adapted to be 40 cm $H_2O$ can be yellow, and/or the cap and/or body for pressure release valves that are adapted to be 60 cm $H_2O$ can be red. The use of color coding can be contrary to the standard approach of color coding components of a respiratory circuit according to the color scheme typically followed for one or more products in a company's business line.

In some embodiments, a pressure release system kit can include a package containing one or more of a pressure release valve with audible apparatus and/or an adapter. In some embodiments, the package can be a bag pouch, box or any package enabling transport of the pressure release valve with audible apparatus and/or adapter. In some embodiments, the pressure release valve with audible apparatus and the adapter can be provided in a sterile form in the package. In some embodiments, the kit can also include information indicative of directions for use of the pressure release valve, audible apparatus and/or adapter, contraindications and warnings, and/or instructions for use of the adapter only with a nasal cannula or other nasal device that is compatible with the adapter.

Figure 7:
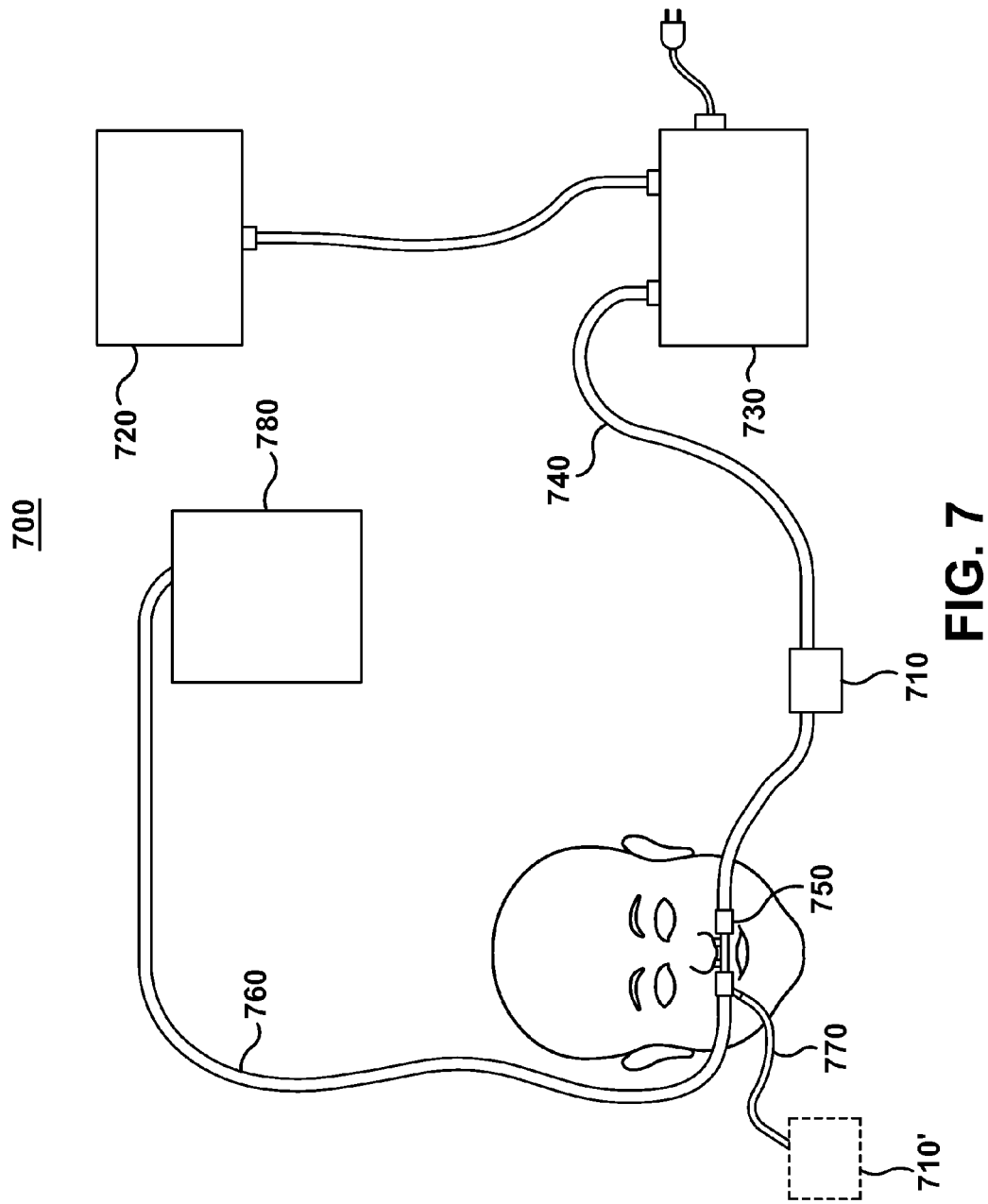
FIG. 7 is a schematic diagram of a respiratory circuit, and patient utilizing the respiratory circuit, according to embodiments of the present invention.

FIG. 7 is a schematic diagram of a respiratory circuit according to an embodiment of the present invention. The respiratory circuit 700 can include a pressure release system 710 (or alternately, 710'). The pressure release system 710, 710' can be any of the aforementioned embodiments of pressure release systems and/or pressure release valves, audible apparatus and/or adapters thereof.

The respiratory circuit 700 can also include a gas source 720, a humidifier 730, an inspiratory tube 740, a respiratory breathing aid 750, and expiratory tube 760, a proximal airway monitoring conduit 770, and/or an exhalatory pressure apparatus 780. The respiratory circuit 700 shown, which includes an exhalatory pressure apparatus 780 for creating backpressure through which a patient must breathe, can be a BNCPAP circuit. However, other circuits such as any continuous positive airway pressure respiratory circuit, high flow respiratory circuit, bi-level respiratory circuit, end/expiratory positive airway pressure respiratory circuit and/or inspiratory positive airway pressure respiratory circuit can also include a pressure release system 710 (or 710') and are encompassed within the scope of embodiments of the invention.

In some embodiments, the gas source 720 can include an oxygen flow meter or a gas blender. The gas source 720 can output gas at any one of various different rates and pressures. By way of example, but not limitation, the gas source 720 can be adapted to output gas at disparate pressure values including, but not limited to, 40 cm $H_2O$ and/or other values less than 100 cm $H_2O$. The respiratory breathing aid 750 can be a nasal cannula, nasal prongs, a face mask and/or a breathing mechanism inserted into the nose or mouth of a patient and/or onto the face of a patient.

In some embodiments, the respiratory circuit 700 can also include a temperature probe adapter (not shown) and/or a pressure gauge adapter (not shown) coupleable to the pressure release system 710. For example, the temperature probe adapter and/or the pressure gauge adapter can be positioned within the path of the inspiratory (or expiratory) limb or extension. In various embodiments, an extension of the respiratory circuit can include a nasal cannula, nasal prongs and/or any other components typically used in a respiratory circuit.

In some embodiments, the gas source 720 can output gas to the humidifier 730 and the humidifier 730 can moisten the received gas and output the received gas to the inspiratory tube 740. The gas can be received by the inspiratory tube 740 and can flow to the pressure release system 710 where the pressure of the gas can be detected. The gas can flow to the pressure release system 710 without intervening elements or via an adapter and/or other tubing. For example, the adapter can be adapter 530, 530' as described above with reference to FIGS. 6A and 6B. As another example, in some embodiments, the gas can be received by a luer having a first end and a second end wherein the first end is coupled to the inspiratory tube 740 and the second end is coupled to the pressure release system.

Referring back to FIG. 7, the pressure release system 710 can detect the pressure of the gas received at the pressure release system 710. If the pressure of the gas is greater than or equal to the activation pressure (or, in some embodiments, if the pressure is greater than or equal to the activation pressure+a margin of error that is +/−5-15% of the activation pressure), the pressure release system can open and/or remain opened and emit the received gas to the environment through the audible apparatus (not shown). When the gas is emitted from the audible apparatus, a sound can be generated. In various embodiments, the sound can be at least one of the following: between 40 and 50 decibels, between 40 and 60 decibels, between 40 and 80 decibels, or at least 40 decibels.

When the pressure of the gas is reduced to, or is maintained at, a value less than the activation pressure, the pressure release valve of the pressure release system 710, can be closed and/or remain closed, and the gas received from the inspiratory tube 740 can be output to the respiratory breathing aid 750, and provided to the patient. Accordingly, the pressure of the gas provided to the patient can be controlled.

In some embodiments, the respiratory circuit 700 can also include a proximal airway monitoring conduit 770 or any number of other adapters, conduits and/or components coupleable to the pressure release system 710'. In this embodiment, the pressure release system 710' can be provided on the portion of the respiratory circuit that receives gas provided from the patient. Accordingly, the pressure of gas provided from a patient can be monitored and/or controlled.

In one embodiment, a healthcare provider can measure the pressure at which the gas source 720 and/or humidifier 730 can output a gas. The provider can select, for use in the respiratory circuit 700, a pressure release system 710 that has the lowest activation pressure above the measured pressure. By way of example, but not limitation, if the gas source 720 outputs gas having a pressure of 35 cm $H_2O$, the healthcare provider can select a pressure release valve having an activation pressure of 40 cm $H_2O$.

In some embodiments, an incubator, or isolette (not shown) or other medical chamber (not shown) adapted to completely or partially enclose a patient can include one or more components of the respiratory circuit 700 but cannot include the pressure release system 710, 710'. The pressure release system 710, 710' can be positioned outside of the incubator or other medical chamber. By way of example, but not limitation, the proximal airway monitoring conduit 770 can have a length such that pressure release system 710, 710' can be positioned outside of the incubator or other medical chamber such that, when the pressure release system emanates the sound alerting the healthcare professionals of excessive pressure, the sound from the audible apparatus is muffled to the patient inside the chamber while being unmuffled to the healthcare professionals outside of the chamber.

The pressure release system 710, 710 can be placed approximately 13 inches from the patient, during use within the respiratory circuit so as to muffle sound to the patient while being proximal to the patient for accuracy in pressure monitoring. As such, the proximal airway monitoring conduit 770 can be approximately 13 inches. In other embodiments, the proximal airway monitoring conduit 770 can be 13 or more inches. In other embodiments, the proximal airway monitoring conduit 770 can be less than 2 feet long.

In conventional systems, in some cases, a pressure release valve is placed four to five feet from a patient. As such, these systems do not provide an accurate measure of the pressure that a patient experiences, and therefore disadvantageously places a patient at risk of exposure to excessive pressure. Further, conventional systems typically provide the pressure release valve on the dry side (i.e., expiratory side or side connected to the inlet, not the outlet, of the humidifier) of a circuit because proximity to the humidifier can affect the operation of the pressure release valve. Accordingly, conventional systems often monitor pressure in the circuit after the patient has been exposed to the pressure and any damage may be done. Further, placement at a distance remote from the patient is typically provided in conventional systems because of the stress placed on the circuit due to the heavyweight of the valves. As such, placement near the patient would not be performed due to the stress and corresponding pull on the circuit at the location proximal to the patient, resulting in potentially pulling the respiratory nasal apparatus out of the nose of the patient and corresponding damage due to lack of gas being provided to the patient.

The embodiments described herein can include placement of the pressure release valve on the inspiratory, i.e., wet side of the respiratory circuit and/or within very close proximity to the patient, as noted above.

In some embodiments, as shown in FIG. 7, the pressure release system 710 can be provided within the patient breathing circuit shown in FIG. 7, and a portion of the inspiratory tube 740 can be provided between the pressure release valve 710 and the respiratory breathing aid 750. The portion of the inspiratory tube 740 provided between the respiratory breathing aid 750, which is connected to the patient, can be of a length allowing the pressure release system 710 to be in close proximity to the patient for accuracy in monitoring the gas pressure that the patient will experience while allowing the pressure release system 710 to be placed outside of an incubator, or isolette (not shown) or other medical chamber such that, when the pressure release system emanates the sound alerting the healthcare professionals of excessive pressure, the sound from the audible apparatus is muffled to the patient inside the chamber while being unmuffled to the healthcare professionals outside of the chamber. By way of example, but not limitation, the length of the portion of the inspiratory tube 740 provided between the respiratory breathing aid 750 and the pressure release system 710 can be approximately 13 inches. In other embodiments, the length can be 13 or more inches. In other embodiments, the length can be less than 2 feet from the patient.

In conventional systems, in some cases, a pressure release valve is placed four to five feet from a patient. As such, these systems do not provide an accurate measure of the pressure that a patient experiences, and therefore disadvantageously places a patient at risk of exposure to excessive pressure. Further, conventional systems typically provide the pressure release valve on the dry side (i.e., expiratory side) of a circuit because proximity to the humidifier can affect the operation of the pressure release valve. Accordingly, conventional systems often monitor pressure in the circuit after the patient has been exposed to the pressure and any damage may be done. Further, placement at a distance remote from the patient is typically provided in conventional systems because of the stress placed on the circuit due to the heavyweight of the valves. As such, placement near the patient would not be performed due to the stress and corresponding pull on the circuit at the location proximal to the patient, resulting in potentially pulling the respiratory nasal apparatus out of the nose of the patient and corresponding damage due to lack of gas being provided to the patient.

Referring back to the embodiments described with reference to FIG. 7, by way of another example, but not limitation, the expiratory tube 750 and/or the nasal cannula can have (or can be coupled to) a conduit having a length such that pressure release system 710, 710' can be positioned outside of the incubator or other medical chamber. As with the foregoing embodiments, the sound of the audible apparatus of the pressure release system that is heard by the patient can be reduced and/or eliminated.

In various embodiments (not shown), the adapter 530, 530' and/or pressure release valve 110, 110', 110", 110'" and/or pressure release system 710, 710' can be employed in third-party respiratory circuits and/or can couple to third-party commercial components of a respiratory circuit (e.g., nasal cannulas, nasal prongs, inspiratory and expiratory limbs adapters and/or various tubing).

For example, a pressure release system such as one or more of the embodiments of the invention described herein can couple within the Salter Labs™ respiratory circuit that includes a nasal cannula and a temperature probe. The Salter Labs™ respiratory circuit can be an HFNC respiratory circuit or any other suitable respiratory circuit dimensioned to be able to couple to the pressure release system. The pressure release system can include an adapter such as one or more of the embodiments of the invention described herein and pressure release valve such as one or more of the embodiments of the invention described herein. The adapter and the pressure release valve can be coupled to one another. In some embodiments, a cap 112, 112' of the pressure release valve can include a flange (not shown) configured to cover an aperture at the top of the cap 112, 112'.

As another example, a pressure release system such as one or more of the embodiments of the invention described herein can couple to a FISHER & PAYKEL® connector. In particular, the adapter 530, 530' can couple to the FISHER & PAYKEL® connector to facilitate respiratory care in a respiratory circuit.

As another example, a pressure release system such as one or more of the embodiments of the invention described herein can be coupled within a respiratory circuit having nasal prongs, a temperature probe, a first inspiratory tube and a second inspiratory tube coupled to the nasal prongs for providing gas to a patient, and an expiratory tube. In this embodiment, the pressure release system can include the adapter 530, 530' coupled between the temperature probe adapter and the second inspiratory tube. The adapter 530, 530' can also be coupled to the first inspiratory tube, which can be coupled to the nasal prongs. The respiratory circuit can be a continuous positive airway pressure respiratory circuit, high flow respiratory circuit, bi-level respiratory circuit, end/expiratory positive airway pressure respiratory circuit and/or inspiratory positive airway pressure respiratory circuit. In some embodiments, one or more of these circuits can be a BNCPAP and/or HFNC circuit.

In some embodiments, with reference to FIGS. 6A and 6B, in embodiments wherein the second connector 534 of the adapter 530, 530' has a 7.5 mm O.D. connection, the second connector 534 can be used in continuous positive airway pressure respiratory circuit, high flow respiratory circuit, bi-level respiratory circuit, end/expiratory positive airway pressure respiratory circuit and/or inspiratory positive airway pressure respiratory circuit to couple tubing, adapters, components and/or other connectors to nasal prongs designed for use in a continuous positive airway pressure respiratory circuit, high flow respiratory circuit, bi-level respiratory circuit, end/expiratory positive airway pressure respiratory circuit and/or inspiratory positive airway pressure respiratory circuit.

As yet another example, a pressure release system such as one or more of the embodiments of the invention described herein can be coupled to respiratory circuit connectors within a respiratory circuit. For example, the adapter of the pressure release system can be coupled to one or more respiratory circuit connectors to facilitate respiratory care.

As yet another example, any of the aforementioned pressure release valves 110, 110', 110", 110''', the pressure release valve in the pressure release system 710, 710' and/or the pressure release system 710, 710' can be sized such that the pressure release valves 110, 110', 110", 110''', the pressure release valve in the pressure release system 710, 710', and/or the pressure release system 710, 710' can couple snugly with the 7.5 mm I.D. connector 532 on the adapter 530, 530' by having one or more portions, or components coupled to such portions that have an O.D. of approximately 7.5 mm. In some embodiments, the coupling can be telescopic coupling. For example, in some embodiments, the component for coupling to the adapter 530, 530' can be the above-described male luer fitting (not shown). The male luer fitting can be coupled to or integrally formed with the pressure release valves 110, 110', 110", 110''', the pressure release valve in the pressure release system 710, 710' and/or the pressure release system 710, 710' such that the pressure release system can be inserted into a standard-sized temperature probe adapter typically found in a respiratory circuit. In some embodiments, the male luer fitting can have an outer diameter (O.D) of approximately 7.5 mm. The small size of the male luer fitting can allow the pressure release valves 110, 110', 110", 110''', the pressure release valve in the pressure release system 710, 710' and/or the pressure release system 710, 710' to fit into the 7.5 mm port of the adapter 530, 530' for use of the pressure release system inline in a respiratory circuit. Various conventional valves and systems cannot be coupled as described above because of the excessive size and weight of the conventional valves and systems and the resultant high likelihood of snagging a patient or healthcare professional or the fabric or clothing associated with each (due to the large size) and/or the stress on the respiratory circuit (due to heavy weight). Each risk results in the conventional system being undesirable for placement inline in the respiratory circuit.

In the embodiments described, the pressure release valves 110, 110', 110", 110''', the pressure release valve in the pressure release system 710, 710' and/or the pressure release system 710, 710' can include a universal 7.5 mm O.D. diameter that can be provided within the port of the adapter 530, 530' typically provided for a temperature probe. In embodiments, the adapter 530, 530' can be designed with different internal and external diameters that vary in size such that the adapter 530, 530' can couple with numerous different third-party pediatric, neonate and/or infant respiratory circuits used for mechanical ventilation, continuous positive airway pressure circuits and/or high flow respiratory circuits.

As described above, the pressure release valves 110, 110', 110", 110''', the pressure release valve in the pressure release system 710, 710' and/or the pressure release system 710, 710' of the embodiments described herein can be lightweight at approximately 10 grams (or approximately 20-25% of the total weight of the conventional valves or systems, which can be 40-50 grams). As also described above, in various embodiments, the pressure release valves 110, 110', 110", 110''', the pressure release valve in the pressure release system 710, 710' and/or the pressure release system 710, 710' can be approximately 1 inch in height, less than 1 inch in height and/or 25-30% of the height of the conventional valves and systems, which can be several inches in height.

Accordingly, the pressure release valves 110, 110', 110", 110''' (or, the pressure release systems 710, 710') can be of dimensions and/or weight that enables the devices to be coupled within a wide of third-party pediatric, neonate, and/or infant respiratory circuits. The coupling can be via the adapter 530, 530'.

Accordingly, the lightweight nature and small size of the pressure release valves 110, 110', 110", 110''', the pressure release valve in the pressure release system 710, 710' and/or the pressure release system 710, 710' can enable it to be placed inline in a respiratory circuit proximal to a patient. In some embodiments, placement proximal to a patient can include placement approximately 13 inches from a patient (such that the pressure release valves 110, 110', 110", 110''', the pressure release valve in the pressure release system 710, 710' and/or the pressure release system 710, 710' can be placed just outside the incubator or isolette of a patient when the patient is a neonate, for example, but remain proximal to the patient). In some embodiments, placement can be less than 2 feet from the patient. In some embodiments, the distance of placement from the patient can be less than 2 feet from the patient. In some embodiments, the distance of placement from the patient can be approximately 20-25% of the circuit between conventional pressure devices and the patient, the distance of which can be approximately four to five feet.

In some embodiments, placement proximal to a patient can include the pressure release valves 110, 110', 110", 110''', the pressure release valve in the pressure release system 710, 710' and/or the pressure release system 710, 710' being coupled to a first end of a tube or other conduit that is coupled to the nasal device of the patient at the second end of the tube or conduit, and wherein the tube or conduit is approximately 13 inches in length. In some embodiments, the length of the tube or conduit can be less than 2 feet from the patient. In some embodiments, the length of the tube or conduit can be approximately 20-25% of the circuit between conventional pressure devices and the patient, the distance of which can be approximately four to five feet.

In some embodiments, the audible apparatus 158' can be designed such that the device emanates a sound upon pressure being greater than or equal to the activation pressure when the device is used inline in a respiratory breathing circuit in operation with a patient when the audible apparatus 158' is placed proximal to the patient. In these embodiments, the audible apparatus 158' can emanate a distinct sound as compared to mere vibrational noise upon pressure being greater than or equal to the activation pressure when the device is used inline in a respiratory breathing circuit in operation with a patient when the audible apparatus 158' is placed proximal to the patient and the length of the respiratory circuit tubing between the gas source and the location of the audible apparatus 158' is more than 1.5 feet. In some embodiments, the conventional pressure devices can emanate vibrational noise, not a clear whistle or horn, being connected to the gas source with tubing of very short length (e.g., 6 inches) and very high flow rates (e.g., greater than 8 lpm). Accordingly, the audible apparatus 158' can emanate sound at much greater distances from the gas source (e.g., coupled to tubing that also couples to the gas source, and is longer than 1.5 feet from the gas source to the audible apparatus 158') and at typical patient flow rates of 1-8 lpm.

In various embodiments, the pressure release valves 110, 110', 110", 110''', the pressure release valve in the pressure release system 710, 710' (including the audible apparatus 158 and/or the adapter 530, 530') can include an audible alert (via the audible apparatus 158' or the audible portion described above), have dimensions for placement in the adapter 530, 530, and/or have the small size and/or weight for placement inline in the respiratory circuit and have placement proximal to the patient.

In some embodiments, the pressure release valves 110, 110', 110", 110''', the pressure release valve in the pressure release system 710, 710' (including the audible apparatus 158 and/or the adapter 530, 530') can be solely mechanical and require no electrical components for operation. As such, the cost can be much lower than valves that involve electronic equipment.

In various embodiments, the pressure release valves 110, 110', 110", 110''', the pressure release valve in the pressure release system 710, 710' (including the audible apparatus 158 and/or the adapter 530, 530') can have the structure and/or function of any of the other embodiments of pressure release valves (including the audible apparatus 158', audible portion, and/or the adapter 530, 530') described herein.

The foregoing description of embodiments of the invention has been presented for purposes of illustration. It is not intended to be exhaustive or to limit the invention to the precise form disclosed, and modifications and variations are possible in light of the above teaching or can be acquired from practice of the invention. Further, one or more components in any of the embodiments can be used in any other embodiment either as an alternative to an existing component and/or in addition to an existing component. The embodiments were chosen and described in order to explain the principles of embodiments of the invention and its practical application. All such variations are envisaged by the inventor and within the scope of the invention.

What is claimed is:

1. A respiratory circuit, comprising:
an adapter having one or more connectors;
a pressure release valve formed with a body portion configured and having a first end of the body portion coupled to one of the one or more connectors of the adapter, wherein the pressure release valve is coupled inline in the respiratory circuit via the adapter, and wherein the pressure release valve comprises an audible apparatus coupled to a second end of the body portion and configured to emanate sound in response to a pressure of a gas received at the pressure release valve being greater than or substantially equal to an activation pressure of the pressure release valve; and
an inspiratory tube having a first end coupled to the adapter.

2. The respiratory circuit of claim 1, further comprising a gas source coupled to a second end of the inspiratory tube.

3. The respiratory circuit of claim 1, wherein the pressure release valve is about one inch or less in height.

4. The respiratory circuit of claim 1, wherein the respiratory circuit is at least one of a continuous positive airway pressure respiratory circuit or a high flow respiratory circuit.

5. The respiratory circuit of claim 1, wherein the pressure release valve is coupled to an inspiratory side of the respiratory circuit.

6. The respiratory circuit of claim 1, wherein the one of the one or more connectors of the adapter to which the body portion is coupled is about 7.5 millimeters in diameter.

7. The respiratory circuit of claim 3, wherein the pressure release valve has a weight less than or substantially equal to about 10 grams.

8. A respiratory circuit apparatus, comprising:
a pressure release valve configured to emanate sound in response to a pressure of a gas received at the pressure release valve being greater than or substantially equal to an activation pressure of the pressure release valve, the pressure release valve also being formed with a body portion configured and having a first end of the body portion coupleable to one of one or more connectors of an adapter configured to be positioned inline in a respiratory circuit, the pressure release valve also comprising an audible apparatus coupled to a second end of the body portion, wherein the audible apparatus is configured to emanate the sound, wherein the pressure release valve is a substantially fixed pressure valve comprising a magnet in the body portion.

9. The respiratory circuit apparatus of claim 8, wherein the audible apparatus being coupled to the second end of the body portion comprises the audible apparatus being molded to the second end of the body portion.

10. The respiratory circuit apparatus of claim 9, wherein at least a portion of the audible apparatus is located within an interior region of the body portion.

11. The respiratory circuit apparatus of claim 8, wherein the sound is at least one of a substantial whistle sound or a substantial horn sound.

12. The respiratory circuit apparatus of claim 11, wherein the pressure release valve is further configured to emanate the sound in response to a flow rate of the gas being less than a defined number of liters per minute.

13. The respiratory circuit apparatus of claim 8, wherein the magnet is configured to open the pressure release valve to allow the gas to enter the body portion and to cause the sound to emanate from the audible apparatus.

14. The respiratory circuit apparatus of claim 8, wherein the pressure release valve is about one inch or less in height and about 10 grams or less in weight.

15. The respiratory circuit apparatus of claim 8, wherein the body portion is dimensioned to telescopically couple to the adapter.

16. The respiratory circuit apparatus of claim 8, wherein the one of the one or more connectors of the adapter comprises a temperature probe connector.

17. A respiratory circuit pressure release system, comprising:
a respiratory circuit pressure release valve configured with at least one port dimensioned to be coupled to an adapter having one or more adapter ports configured to couple the adapter to a respiratory circuit, wherein the pressure release valve is coupleable in series in the respiratory circuit via the adapter, and wherein the pressure release valve comprises an audible apparatus configured to emanate a sound in response to a pressure of a gas received at the pressure release valve being greater than or substantially equal to an activation pressure of the pressure release valve, wherein the pressure release valve comprises at least one of a compression spring or a magnet.

18. The respiratory circuit pressure release system of claim 17, further comprising the adapter.

19. The respiratory circuit pressure release system of claim 17, wherein at least one of the compression spring or the magnet is configured to open the pressure release valve to allow the gas to enter the pressure release valve and to cause the sound to emanate from the audible apparatus.

* * * * *